US005528046A

United States Patent [19]

Ishikawa

[11] Patent Number: 5,528,046
[45] Date of Patent: Jun. 18, 1996

[54] METHOD AND DEVICE FOR DETERMINING THE LOCATION AND NUMBER OF FLUORESCENT MOLECULES

[75] Inventor: Mitsuru Ishikawa, Hamamatsu, Japan

[73] Assignee: Hamamatsu Photonics K.K., Hamamatsu, Japan

[21] Appl. No.: 149,840

[22] Filed: Nov. 10, 1993

[30] Foreign Application Priority Data

Nov. 10, 1992 [JP] Japan .................................. 4-300134

[51] Int. Cl.⁶ .................................................. G01N 21/64
[52] U.S. Cl. .................................................. 250/461.2
[58] Field of Search ........................................ 250/461.2

[56] References Cited

U.S. PATENT DOCUMENTS

| | | | |
|---|---|---|---|
| 4,962,037 | 10/1990 | Jett et al. | 435/6 |
| 5,062,942 | 11/1991 | Kambara et al. | 204/299 |

FOREIGN PATENT DOCUMENTS

| | | |
|---|---|---|
| 8116691 | 5/1992 | Australia . |
| 0440342 | 8/1991 | European Pat. Off. . |
| 0469444 | 2/1992 | European Pat. Off. . |
| 0541296 | 5/1993 | European Pat. Off. . |
| 0556509 | 8/1993 | European Pat. Off. . |
| 2-168161 | 6/1990 | Japan ................... 250/461.2 |
| 3-502041 | 5/1991 | Japan . |
| WO8903432 | 4/1989 | WIPO . |
| 9014589 | 11/1990 | WIPO . |
| 9218608 | 10/1992 | WIPO . |

OTHER PUBLICATIONS

Brocklehurst et al, "Luminescence of DNA Excited in the Vacuum Ultraviolet", Chemical Physics Letters, vol. 173, No. 1, Sep. 28, 1990, pp. 129–131.

Tsuyoshi Hayakawa, Single Photon Imaging, Image Analysis in Biology, 1991, pp. 76–86 (CRC Press).

W. P. Ambrose, Th. Basche, W. E. Moerner, Detection and spectroscopy of Single Pentacene Molecules in a p–Terphenyl Crystal By Means of Fluorescence Excitation, J. Chem. Phys. 95(10), Nov. 15, 1991, pp. 7150–7163.

R. A. Mathies, Konan Peck, L. Stryer, Optimization of High–Sensitivity Fluorescence Detection, Anal. Chem. vol. 62, No. 17, Sep. 1, 1990, pp. 1786–1791.

K. C. Ng, W. B. Whitten, S. Arnold, J. M. Ramsey, Digital Chemical Analysis of Dilute Microdroplets, Anal. Chem. vol. 64, No. 23, Dec. 1, 1992, pp. 2914–2929.

J. H. Hahn, S. Soper, H. Nutter, J. Martin, J. Jett, R. Keller, Laser–Induced Fluoescence Detection of Rhodamine–6G at $6 \times 10^{-15}$M, Applied Spectroscopy vol. 45, No. 5, 1991, pp. 743–746.

S. Soper, L. Davis, E. Shera, Detection and Identification of Single Molecules in Solution, J. opt. Soc. America vol. 9, No. 10, Oct. 1992, pp. 1761–1769.

(List continued on next page.)

*Primary Examiner*—Constantine Hannaher
*Attorney, Agent, or Firm*—Cushman, Darby & Cushman

[57] ABSTRACT

The present invention is directed to a device and method for determining the presence of fluorescent molecules, locations thereof, and number of fluorescent molecules in a local area irradiated with excitation light based on the number of fluorescence photons generated per unit period of time by the irradiation of the excitation light counted as a quantized fluorescence intensity of the fluorescence molecules and a distribution of appearance frequencies of the fluorescence photons formed on a two-dimensional image. In accordance with the present invention, a device is provided which comprises a light source for irradiating excitation light to a local area on a flat substrate with the adsorbed fluorescent molecules, and fluorescence detecting means for detecting fluorescence photons from the fluorescent molecules and for forming a distribution of appearance frequencies of the fluorescence photons per unit period of time on a two-dimensional image corresponding to the local area.

17 Claims, 18 Drawing Sheets

OTHER PUBLICATIONS

M. Orrit, J. Bernard, Single Pentacene Molecules Detected by Fluorescence Excitation in a p–Terphenyl Crystal, Physical Review Letters, vol. 65, No. 21, Nov. 19, 1990, pp. 2716–2719.

P. DiLazzaro, P. Mataloni, F. DeMartini, Orientation of Xanthene Adsorbate Molecules at Dielectric Interfaces, Chemical Physical Letters, vol. 114, No. 1, Feb. 15, 1985, pp. 103–108.

T. F. Heintz, C. K. Chen, D. Ricard, Y. R. Shen, Spectroscopy of Molecular Monolayers by Resonant Second–Harmonic Generation, Physical Review Letters, vol. 48, No. 7, Feb. 15, 1982, pp. 478–481.

METHOD AND DEVICE FOR DETERMINING THE LOCATION AND NUMBER OF FLUORESCENT MOLECULES

BACKGROUND OF THE INVENTION

1. Field of the Invention

This invention relates to a method and a device for optically discriminating nucleic acid bases (e.g., nucleotides) constituting a gene and for determining a sequence of the nucleic acid bases. The present invention specifically relates to an art in which fluorescence or luminescence of fluorescent molecules represented by the bases is utilized to discriminate the number, position, etc. of fluorescent molecules.

2. Related Art

DNA (deoxyribonucleic acid containing a base as a main component, with sugar and phosphoric acid bonded to the base), which is a composition material of a gene, exists as a strand of base pairs in a double helical structure. The double helix contains genetic information in code-like form (i.e., a base sequence). Genes are gathered in strings in the cell nucleus. Lower organisms, such as microorganisms, have thousands of nucleotide pairs at most, but higher organisms having more genetic information have several billion to an estimated 29 billion base pairs.

Genetic information is determined by a sequence of four kinds of bases—adenine (A), guanine (G), cytosine (C), and thymine (T). Accordingly, it is of great significance to know the base sequences for the future development of such fields as genetic engineering, medicine, etc.

It is known that these bases emit an intrinsic fluorescence, which increases at low temperatures (e.g., 100 K or less). It is possible to discriminate the bases in principle by examining their fluorescent lifetimes. To generate fluorescence, it is necessary to irradiate the bases with excitation light. A high sensitivity detector, such as a photomultiplier, is suitable for detecting fluorescence. The apparatus disclosed in, e.g., "Proc. Natl. Acad. Sci.", U.S.A., 86 (1989) 4087–91 (a first conventional method) is known for detecting a single fluorescent molecule. In this reference, as shown in FIG. 1, excitation light (laser beam) from a light source is applied to a flow cell 61 containing dye solution. Fluorescence is detected by a photomultiplier 63 in a direction which is normal to both the direction of irradiation of the excitation light and the direction of flow of the dye solution.

In FIG. 1, an optical system for forming an image on the photomultiplier 63 comprises a lens 64, an aperture 65, a wavelength selecting filter 66, and a condensation lens 67. A measuring system for measuring the fluorescence detected by the photomultiplier 63 comprises an electric signal detecting/multiplying unit 68, a fluorescent photon counter 69, and a computer 70.

A second conventional method in which respective single-fragment bases are modified by fixable fluorescent dyes is disclosed in Japanese Patent Laid-Open Publication No. 100945/1991, U.S. Pat. No. 4,962,037. This second conventional method has the same arrangement in which the respective bases are labelled by their characteristic dyes and then cut off by exonuclease III. A sequence of the bases is determined based on difference in fluorescence spectrum.

A third conventional method for single fluorescent molecule detection relies on high resolution spectroscopy of a single impurity aromatic molecule (pentacene) embedded in an organic molecule (paraterphenyl). This third conventional method, which is disclosed in J. Chem. Phys. 95(10), 15 Nov. 1991, 7150–7163, is not suitable for detecting the base. However, this method measures a fluorescence excitation spectrum of pentacene at ultra-low temperature (about 4K) to measure a uniformly wide spectrum in a non-uniformity wide spectrum, thereby using the former as a fluorescence spectrum of the single molecule.

On the other hand, advantages of the first conventional method produced by using a flow cell 61 are that degradation of dyes can be suppressed and that a filter can be provided in a dye circulation system to remove dust. But fluorescence can be observed only in the limited period of time (about 1 μsec) in which the molecule is passing through a region irradiated with the excitation light. Accordingly, in the device of FIG. 1, the fluorescence from the bases of genes cannot be correctly and efficiently detected. Although only four kinds of bases (A, G, C, and T) are contained in DNA, a large quantity of each kind of base is present. However, because their sizes are very small, fluorescence generated from these bases is very feeble. Consequently, it is very difficult to discriminate type of bases solely on the basis of the short fluorescence observation period.

A longer period of fluorescence emission and higher efficiency can be obtained by irradiating the excitation light to a base flow over a larger area in the direction of the base flow. But in this case, the bases in the base flow are simultaneously detected, making the processing of the obtained data difficult.

SUMMARY OF THE INVENTION

The present invention is directed to a method for determining a sequence of the bases (A, G, C, and T) constituting a single fragment of nucleic acid. An object of the present invention is to provide a method for speedily and accurately discriminating types of bases. To practice this method, the present invention provides an optical discriminating device for detecting fluorescence or luminescence of fluorescence molecules.

The device for determining a location of a molecule-group and the number of fluorescence molecules in the molecule-group according to this invention comprises a light source (e.g., a laser device) for irradiating excitation light to a local area on a flat substrate with a group of adsorbed fluorescent molecules. The device further includes a fluorescence detecting means for detecting fluorescence photons generated by irradiating the excitation light to a local area on the substrate and for measuring the number of fluorescence photons per unit period of time as a quantized fluorescence intensity of the molecule-group.

Here quantization includes "to express as multiples of a definite quantity".

The present invention is further directed to a method for determining the location of a molecule-group and the number of fluorescent molecules in the molecule-group.

In accordance with this method, the present invention provides for a fluorescence detecting means disposed at a position outside the optical paths of the excitation light from the light source and of reflected light on the surface of the substrate. The fluorescence detecting means includes an optical microscope (variable magnification) for condensing fluorescence in a local area on the surface of the substrate. The fluorescence detecting means further includes a photon counting system for counting fluorescence photons condensed by the optical microscope and for displaying an appearance frequency distribution of fluorescence photons on a two-dimensional image corresponding to the local area.

In particular, the photon counting system forms the appearance frequency distribution of the fluorescence photons in the unit period of time by plotting the frequency of the appearance of the fluorescence intensities in the fluorescent spots on a two-dimensional image of the sample substrate. The number of fluorescent molecules in the fluorescent spots is identified based on the appearance frequency distribution of the fluorescence photons per unit period of time displayed on the two dimensional image.

Furthermore, the device may comprise moving means (i.e., an X–Y stage) for relatively moving the local area on the substrate. The X–Y stage horizontally moves with respect to the fluorescence detecting means. The moving means further comprises a rotary stage supported by the X–Y stage for fixing the substrate.

A specimen (substrate) with a molecule-group comprising fluorescent molecules adsorbed thereon is prepared by spraying a solution containing the fluorescent molecules in a fine liquid droplet, affixing the fine liquid droplets to the surface of the flat substrate, and then drying the substrate at room temperature or less.

The fluorescent molecules contained in the solution include a complex of a protein and a predetermined number of substances emitting fluorescence. The solution containing the fluorescent molecules is formed by an ultrasonic wave into a fine liquid droplet containing the molecule-group. It is preferred that the molecule-group includes four fluorescent molecules or less as the average number of fluorescent molecules. The substrate on which the molecule-group is adsorbed includes a silicon wafer and may be disk-shaped.

A reason for allowing the substrate to naturally dry is that Raman scattering of the solvent, which is one cause of background light, is reduced in comparison with that in the solution. Moreover, reactions between the solvent and the molecule, which can deteriorate the fluorescent molecule (e.g., a dye molecule), can be largely prevented. Heating and vacuum drying can remove a fluorescent molecule from the substrate.

The device for determining the sequence of bases of nucleic acid according to this invention comprises a light source for irradiating a pulsed excitation light to a local area where a base is present, a flat substrate with a sequence of bases of the nucleic acid, a fluorescence detecting means for detecting the fluorescence generated from the sequence of bases present in the local area on the flat substrate and for identifying the sequence of bases based on a wavelength distribution of the fluorescence and lifetime of the fluorescence, and a moving means for moving the local area on the flat substrate along the sequence of the bases.

The fluorescence detecting means can include a photon counting system for determining the location of a base in the local area.

The above-described device enables this method for determining a sequence of bases of a nucleic acid according to this invention to be practiced.

An additional characteristic of the present invention is that the substrate is a disk-shaped silicon wafer. This allows for the downsizing of the device. Cooling means may be included for increasing fluorescence intensities, thereby encouraging the detection of fluorescence of the respective bases.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

As described above in connection with the related art, development of a method and device for measuring the location and the number of fluorescence molecules has until now proven unsuccessful. Accordingly, providing a method for detecting locations of fluorescent molecules and for measuring the number of fluorescent molecules is an important part of the present invention. The method and device for practicing the method as provided by the present invention will be explained below.

One characteristic of this invention is that for confirming the presence of a molecule-group comprising fluorescent molecules, excitation light is irradiated to count the number of generated fluorescent photons per unit time as quantized fluorescence intensity in proportion to the number of fluorescent molecules. A location (a fluorescent spot) of a molecule-group and the number of fluorescent molecules in the molecule-group present in a local area irradiated with the excitation light is determined based on an appearance frequency distribution of the quantized fluorescence intensity formed on a two-dimensional image.

Figure 2:
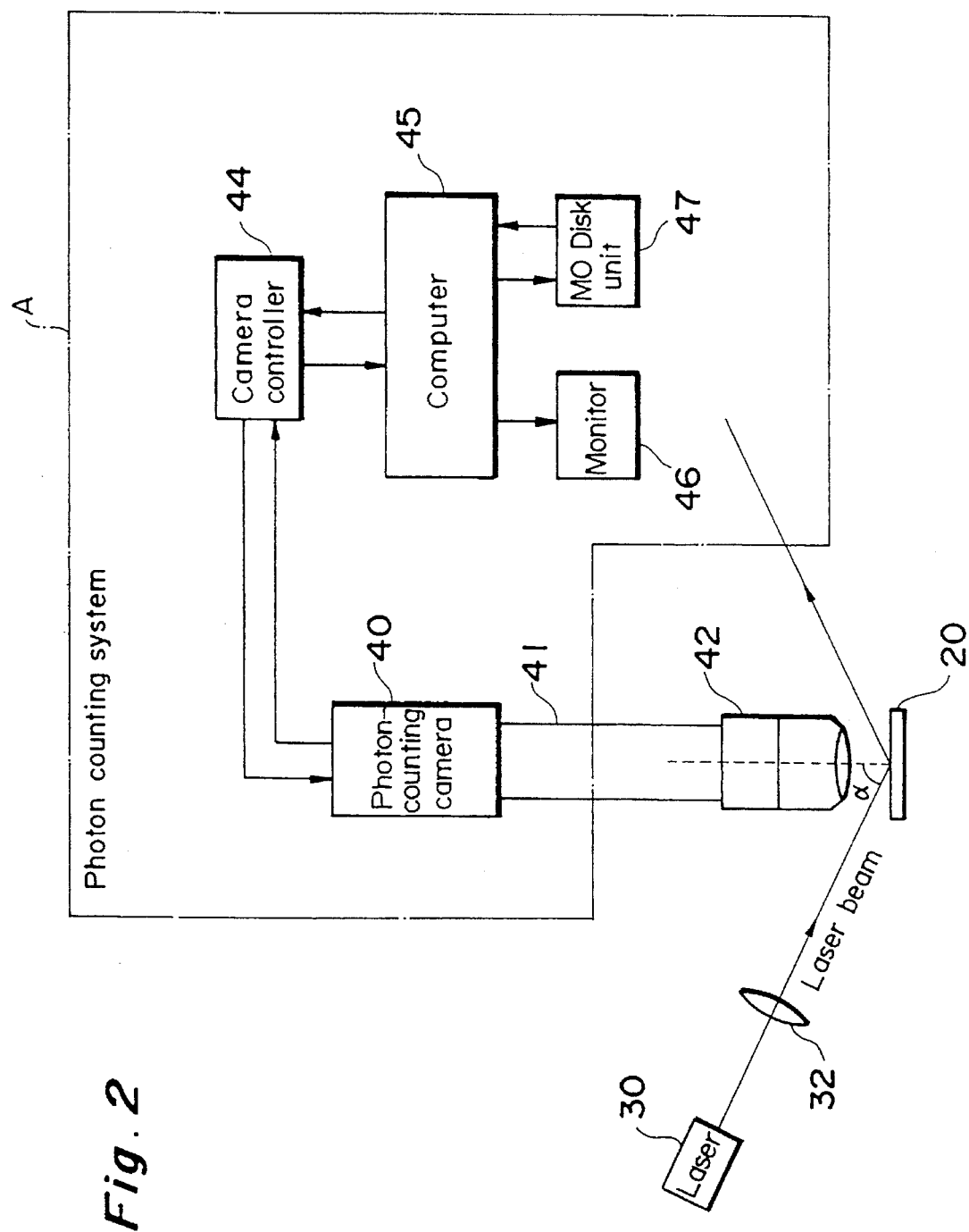
FIG. 2 is a diagrammatic view of the device for determining a location of a molecule-group and the number of fluorescent molecules in the molecule-group according to this invention.

FIG. 2 is a block diagram of an exemplary device for practicing a method for detecting a molecule-group comprising fluorescence molecules according to the present invention. This device comprises an excitation light source 30 for irradiating excitation light to the surface of a silicon wafer as a substrate 20 with the molecule-group to be measured adsorbed thereon (this silicon wafer is covered with an insulating natural oxide layer), an optical microscope objective 42 for condensing fluorescence generated from the fluorescent molecules in the molecule-group, and a photon counting system A (comprising a photon-counting camera 40, camera controller 44, computer 45, a monitor 46, and MO disk unit 47) for detecting at an excitation light irradiating position the fluorescence from the fluorescent molecules. The optical microscope objective 42 and the photon counting system A are connected by a microscope body 41. The substrate 20 is positioned in a clean booth of Class 1000 or less, so as to be in a clean ambient atmosphere. This device can be used not only for a base of nucleic acid, but also for various substances, including protein, so long as the substance generates fluorescence. A molecule which does not generate fluorescence can be bonded with a predetermined number of substances emitting fluorescence to be measured by this device.

It is preferable that the excitation light source 30 continuously irradiate intense light (e.g., coherent laser beam) to a part of the substrate 20 upon which the molecule-groups comprising fluorescent molecules are adsorbed. Here, a 488 nm-wavelength argon laser beam (Spectra-physics 2030) is adjusted by a calibrated power meter (Spectra-physics 385) to have an average power of 7–20 mW. Then, the beam is condensed by a lens 32 with a 50 cm focal length. The excitation light source 30 is arranged so that excitation light enters at an angle (slantly) $\alpha=70°$ as shown in FIG. 2, so that the reflected beam on the surface of the substrate 20 reflects at an angle (slantly).

The flat substrate 20 is now described in greater detail. According to the results of the embodiments (e.g., FIG. 17) which will be explained later, an intensity ratio between a fluorescence intensity and a background light intensity is about 100:1. The intensity ratio is preferably larger. In the following embodiments, an irradiation angle is about 20° to the horizontal plane; however, the irradiation angle is not limited to this particular angle so long as the laser beam (excitation light) and the reflected beam are not directly irradiated to an objective (incorporated in the optical microscope 42) for condensing the fluorescence and can illuminate a set local area of the substrate 20.

Hereinafter, the term "flat" is defined as a state in which the fluorescence can be measured at an intensity ratio of above 10:1 with respect to the fluorescence and background light when the laser beam is incident on the surface of the substrate 20 at an irradiation angle which meets the above-described conditions.

A background light intensity is evaluated in a photon count value (the number of fluorescent photons per unit time) in an area on a two-dimensional image where a fluorescence spot (i.e., a pixel group corresponding to a position on the substrate 20 where the fluorescence is detected and which indicates the location of the molecule-group to be measured) is absent, and which has the same area as the fluorescence spot.

An intensity ratio between the fluorescence and the background light is limited to 10:1 or more to limit the average number of fluorescent molecules contained in one liquid droplet (referred to as a molecule-group) to below four (4) so as to facilitate the discrimination of the individual molecules. That is, the probability of one liquid droplet containing many (e.g., ten) fluorescent molecules in a Poisson distribution having an average number of 4 cannot be ignored. Even in such case, the fluorescence and the background nonetheless can be discriminated from each other by setting the intensity ratio between the fluorescence and the background light at 10:1 or more.

The photon counting system A is a system for detecting the location of the molecule-group adsorbed on the substrate 20 and the number of fluorescent molecules at the location. The photon counting system A must be capable of detecting feeble light. In this embodiment, the system A is an imaging/image analyzing system (ARGUS 50 VIM 3, by Hamamatsu Photonics K.K.) with the optical microscope 42 mounted on the microscope shaft 41, which can detect the feeble light by two-dimensionally counting the fluorescent photons. In this embodiment, the optical microscope 42 for condensing fluorescence from the fluorescent molecules includes an objective (OPTIPHOT XP, by NIKON) with a magnification of 40 (0.55 NA) or 100 (0.75 NA). An exemplary 100× objective is a NIKON CF M plan SLWD, NA=0.75 having a working distance (WD) of 4.3 mm. This 100×objective was used in the experiment using disodium fluorescein (DFL). The 40×objective was used for the droplet size determination shown in FIGS. 12–14, and for the experiment using streptoavidine-dye complex.

The operation principle of the photon counting system A is described by T. Hayakawa: Image Analysis in Biology, ed. D.-P. Hader, Chap. 5, pp. 75–86 (CRC Press, Boca Raton, 1992).

The photon-counting camera 40 has 512×512 pixels and high sensitivity (VIM 3). One pixel has a 0.3 μm-width for the 40-magnification objective and 0.12 μm-width for the 100×objective. The fluorescence from the fluorescent molecules is converted into an image signal by the photon counting camera 40. The signal is stored (counting the fluorescent photons), image-processed, recorded, and image-displayed by a camera controller 44, a personal computer 45, a MO disk unit 47, and a monitor 46, respectively.

Figure 4:
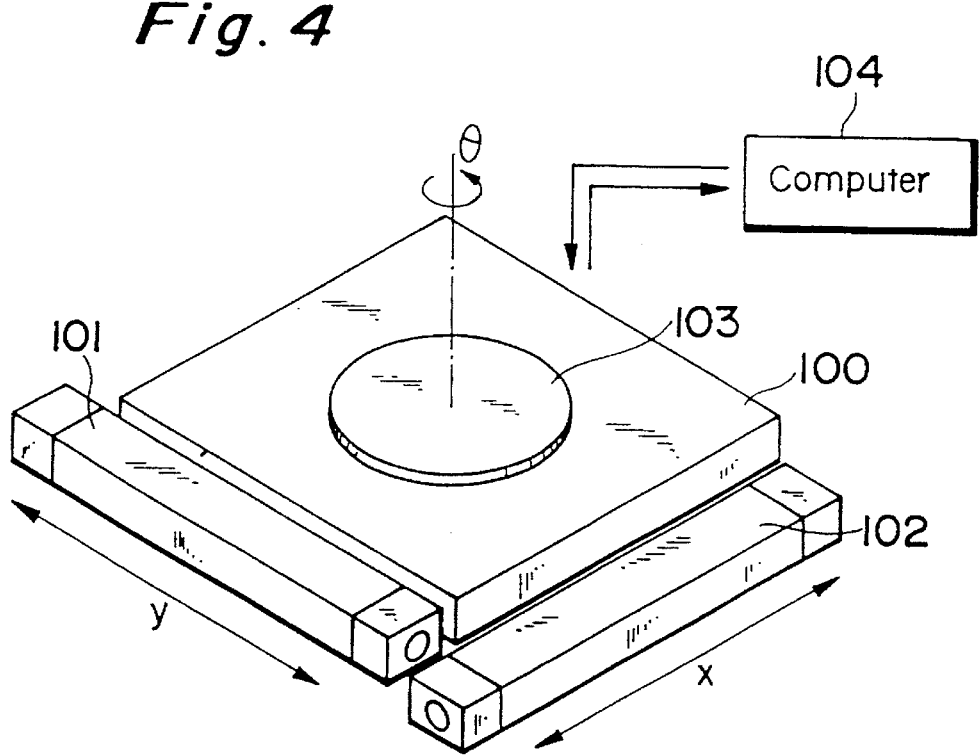
FIG. 4 is a diagrammatic view of moving means for moving the substrate as shown in FIG. 3.

The position and rotation of the substrate 20 is controlled by a drive device (moving means), as shown in FIG. 4. A relative position of a local area of the surface of the substrate 20 can thereby be controlled to be in the field of the optical microscope 20 and the photon counting camera 40.

As shown in FIG. 4, the drive device horizontally moves an X–Y stage 100 by first and second pulse motors 101, 102 in the x-direction and y-direction. A rotary stage 103 fixing the substrate 20 is mounted on the X–Y stage 100. The local area of the substrate 20 can be moved in the x-, the y-, and θ-directions. These parameters x, y, θ can be independently controlled by a computer 104, whereby a position where a liquid droplet containing a molecule-group adsorbed on the substrate 20 can be spirally displaced (according to the embodiments which will be explained later).

The above first and second pulse motors 101, 102 are known and can control displacements in the x- and y-directions by a minimum unit of 1 μm (MSS-150/200, Microscanning stage, 1993, vol. 1, CHUO PRECISION INDUSTRIAL CO., LTD - CATALOG).

Figure 1:
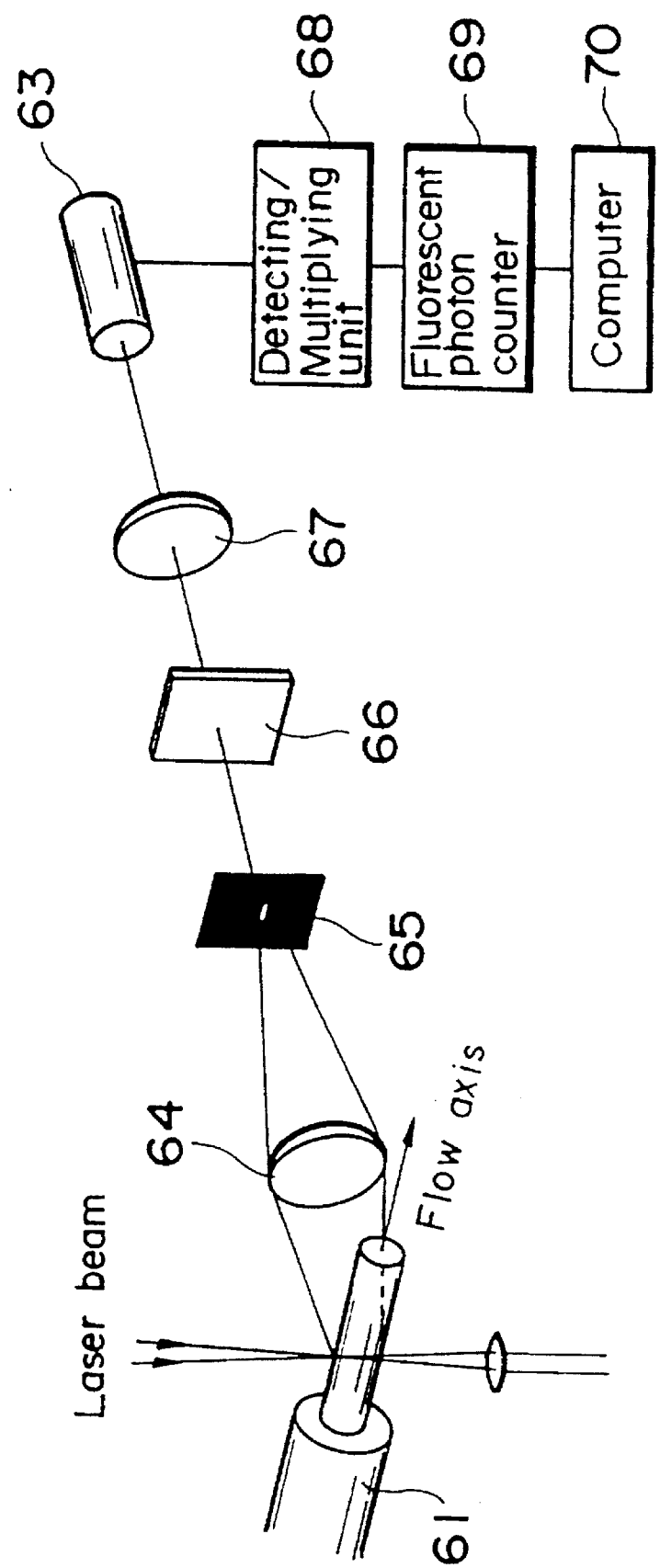
FIG. 1 is a diagrammatic view of a proposed conventional device for determining a sequence of bases of a nucleic acid.

It is possible to provide wavelength selecting optical components for screening out light other than the fluorescence intrinsic of an object to be measured in the microscope body 41 between the light detecting surface of the photon-counting camera 40 and the optical microscope 20 so as to prohibit incidence of scattered light from the excitation light. As in FIG. 1, the wavelength selecting means comprises a wavelength selecting filter (for example the color filter BA 520–560, by NIKON) and a dichroic mirror (for example DM-510, by NIKON). The type of mirror and filter selected depends on the color of fluorescence. In this embodiment, BA520–560 and DM-510 are used because fluorescence spectrum of DFL has a 520 nm-maximum wavelength. The positioning of the laser beam outside of the microscope field can prohibit the incidence of background and scattered light due to the laser on the surface of the substrate 20. Approximately 60% of the fluorescence photons from DFL pass through the combination of the filter and the mirror.

Next, the method for determining the location of the molecule-group and the number of fluorescent molecules in the molecule-group by this device will be explained in the sequence of the steps thereof.

Figure 3:
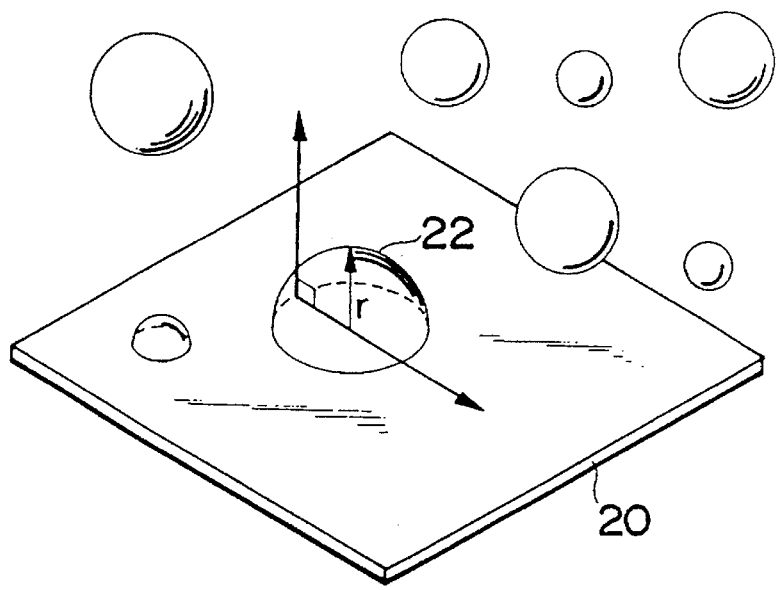
FIG. 3 is a view of a fine liquid droplet 22 containing the molecule-group to be adsorbed on a silicon wafer as a flat substrate.

The fluorescent molecules to be measured are dissolved and diluted in a predetermined solvent. This solution is adsorbed on the surface of the substrate 20 in atomized condition (fine liquid droplets) (FIG. 3). Then the substrate 20 is dried in a clean atmosphere to prepare the substrate 20 with the adsorbed molecule-groups. The solvent has high purity. One or more liquid droplets are positioned in a view area of the microscope substantially corresponding to the resolution of the microscope objective 42 (an average number of fluorescent molecules (i.e., molecule-group) in one liquid droplet is 4 or less) (this will be explained later). Drying of the solvent decreases Raman scattering of the solvent which is one cause of background light. In addition, chemical reactions between the solvent and the fluorescent molecules, which can degrade fluorescent material, is greatly hindered by drying. Allowing the solvent to dry naturally (i.e., dry naturally) is preferred over heat drying or vacuum drying, which will remove the specimen molecules. If a silicon wafer is used as the substrate 20, the fluorescent molecules are fixed by absorption, and the fluorescent molecules cannot be easily dissociated. Accordingly, the substrate 20 with fluorescent molecules can be repeatedly measured as a record medium. The silicon wafer as the substrate 20 is used as supplied and its surface is covered with insulating native oxide ($SiO_2$). Furthermore, the reflectivity of the substrate 20 (40%) can be measured with an Xe lamp coupled with a green interference filter (520 nm) and a power meter can be equipped with an integration sphere (UDT S370).

An average number of the fluorescent molecules contained in the liquid droplet 22 is determined by the concentration of the solution containing the fluorescent molecules and the droplet size. Accordingly, when the size of the liquid droplet 22 is assumed constant, the average number of the fluorescent molecules in one liquid droplet 22 can be controlled by changing the concentration of the solution. By controlling the concentration, the size of the liquid droplet 22 can be arbitrarily set, unless the liquid droplet 22 is so large as to be outside the visual field of the detecting means.

Figure 12:
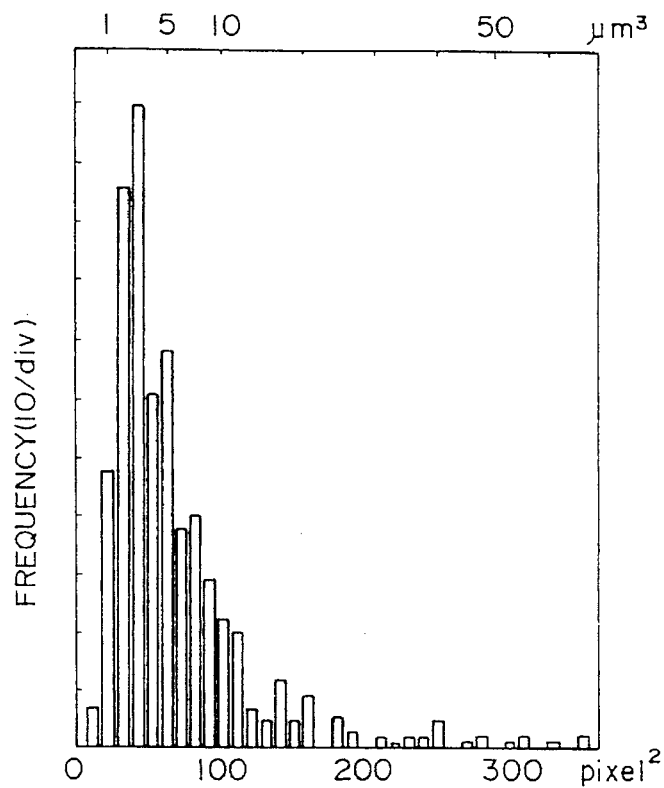
FIGS. 12–14 are views of distributions of an area on the surface of the substrate occupied by one of the liquid droplets containing a fluorescence molecule when their atomizing time is 10 seconds (FIG. 12), 7 seconds (FIG. 13), and 3 seconds (FIG. 14), respectively.
Figure 13:
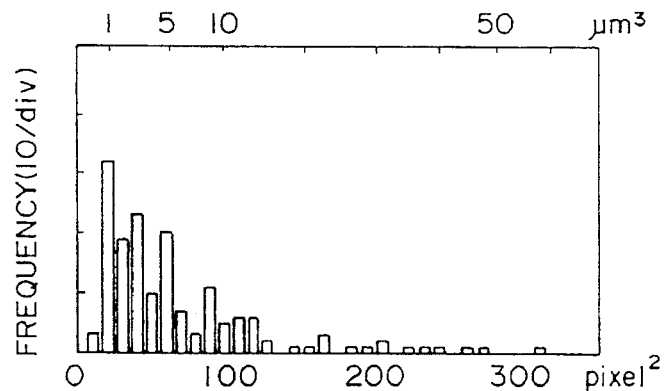
Figure 14:
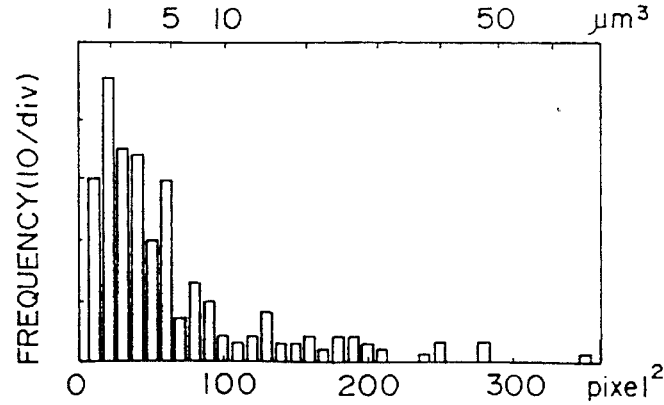

In the embodiments which will be explained later (for example, FIGS. 12–14), the liquid droplets 22 do not have constant sizes; rather, distributions appear in the size of droplets 22 (FIGS. 12–14 are results of the inventor's evaluation of the distributions). The distributions show that the liquid droplets 22 of volumes of 10 $\mu m^3$ or less account for 90% or more of the liquid droplets. Since the present invention according to this embodiment can prepare liquid droplets 22 having a volume of 10 $\mu m^3$ or less, it is easy to calculate a solution concentration which allows one liquid droplet to have an average number of fluorescent molecules of 4 or less. In computation, one liquid droplet can have an average number of four (4) by setting the concentration of the solution containing the fluorescent molecules at 0.68 nano mol/liter or less.

A reason for limiting an average number of fluorescent molecules in the one liquid droplet to 4 is to facilitate discrimination of the fluorescent molecules. That is, when one liquid droplet having a set volume has an average number of fluorescent molecules of 5 or more, it is very difficult to discriminate a Poisson distribution contour (i.e., a contour of a graph plotting probabilities of the number of fluorescent molecules appearing with respect to the number of fluorescent molecules). For example, it is easier to discriminate the Poisson distribution contour with one average molecule from that with two average molecules than to discriminate the Poisson distribution contour with 5 average molecules from that with 6 average molecules.

Then, the substrate 20 is set in the device of FIG. 2. While the laser beam is irradiating, light emissions from a specific area on the substrate 20 are measured. Since the laser beam is incident and reflected slantly, the light emissions do not enter a field of the optical microscope 42 and the effect of the background light is very small. In particular, the substrate 20 is a silicon wafer; the scattered light has a small intensity because of a high speculum degree of the surface thereof. Furthermore, since no solvent molecules are on the surface of the substrate 20, there is little Raman scattering and the background light has a small area, which allows fluorescence from one molecule to be detected. The photon counting system A can measure fluorescence intensity (the number of the fluorescence photons per unit time) and fluorescent spots where fluorescence of the intensity appears (an area where the fluorescent spots are present) on each screen corresponding to each local area, whereby it can detect the quantity and position of the fluorescent molecules.

In the embodiments which will be explained later (e.g., FIG. 2), an irradiation angle of the laser beam to the substrate 20 is set at $\alpha=70°$, and an intensity ratio between the fluorescence and the background light is higher than 100:1.

This detection of fluorescent molecules will be detailed based on actual measured results.

The light detecting efficiency can be positionally dependent sometimes occurs because of uneven irradiation by laser beams ($TEM_{00}$ mode) to the substrate 20. This is measured beforehand. A sheet of opaque glass is placed at a position where the substrate 20 is to be set to observe scattering of the laser beam of 488 nm wavelength. Significant portions of 512×512 pixel area are marked. A brightness difference of the effective parts is about ±5% at most when the 100×, NA=0.75 objective is used. In this embodiment, the laser-beam diameter on the surface of the substrate 20 is estimated to be 300 μm ($1/e^2$) and the field of vision in the photon counting system A is approximately 60 μm in diameter when the 100×, NA=0.75 objective is used.

Here, the fluorescent molecules to be measured are provided by complexes of protein and fluorescent substance. The fluorescent substance is fluorescein biotin (FLB) and disodium fluorescein (DFL). FLB and DFL have, in an aqueous solution, a 489 nm absorption peak ($\epsilon=90,000$ $cm^{-1}M^{-1}$ at pH=8.4) and a fluorescence maximum at 520 nm (fluorescence quantum yield of $\Phi_f=0.95$ at pH=8.4 which were measured values given by Hitachi 557 and Hitachi 850). The protein used is tetrameres of streptavidin (SA) (the molecular weight 4×15,000). This SA has high affinity (dissociation constant $k_d=10^{-15}M^{-1}$) with FLB. A part (B) of FLB specifically reacts with SA, and 4 FLB/B molecules can be bonded (avidin-biotin complexes are produced). This reaction can be used to control the number of fluorescent substances which bond with SA. By controlling a mixed ratio (mole ratio) of FLB/B, the number of FLB molecules which bond with SA can be manipulated to be between 1 and 4.

At first, the solution containing the above-described fluorescent substance to be measured is atomized to form liquid droplet 22 to be adsorbed on the substrate 20 (FIG. 3), and the substrate 20 is thereafter dried. The substrate 20 is thus prepared. In this embodiment, an ultrasonic humidifier (Sharp HV-A 200) was used to atomize the sample solution into fine liquid droplets 22, and the drying was conducted in a clean ambient atmosphere. Natural drying of the solvent reduces the Raman scattering of the solvent; decreased scattering causes a decrease in background light. Solvent in solution causes more Raman scattering than dried solvent. In addition, the reaction of the solvent with the fluorescent molecules, which is a cause of degradation of the fluorescent substance, can be drastically prohibited. By contrast, it is very possible that heating and/or vacuum-drying (as opposed to natural drying) will remove the fluorescent molecules (the molecule-groups) to be measured.

As seen in the embodiments which will be explained later (e.g., FIG. 17), a distribution of sizes (volume) of the liquid droplets 22 reveals that 90% or more of the liquid droplets have a volume of 10 $\mu m^3$ or less. The maximum number of occurrences in the size distribution is in a range of 3–4 $\mu m^3$. In this embodiment, as described above, the fine liquid droplets 22 are produced by means of the ultrasonic humidifier. Other exemplary liquid droplet generators are described in, e.g., Kin C. N., "Digital Chemical Analysis of Dilute Microdroplets", Anal Chem., b 1992, 64, 2914–2919.

In this embodiment (FIG. 3), the volume for each liquid droplet 22 is calculated on the assumption that the liquid droplet 22 is hemispherical and has a 90° contact angle. It is assumed that a fluorescent area (a fluorescent spot) after drying is in an equatorial plane of a hemispherical liquid droplet.

The above-described solution is diluted with super-pure water (Mili-Q water, Milipore). The solution can have a nano-mol/liter concentration, and as will be explained later, the average number of fluorescent molecules in one liquid droplet containing one molecule-group can be calculated. Some specimen aqueous solutions were repeatedly atomized onto silicon wafers (the substrate 20), dried, and measured at 296K. The aqueous solutions atomized onto the silicon wafers were prepared as follows.

SA was dissolved in a mixed aqueous solution (pH 7.5) of 10 mM of phosphate and 0.15M of NaCl (2 mg/ml), and FLB and B were dissolved in the same buffer solution (phosphate and NaCl). Four kinds of mole ratios of FLB to B (4:0, 3:1, 2:2, and 1:3) were prepared. A molar ratio which enabled FLB and SA to sufficiently react with each other was 20:1. The four kinds of FLB/B solutions were mixed in 100 μl of SA solution. Then, the above-described buffer solution was added to prepare a 200 μl solution.

After the thus-prepared solution was allowed to stand at 277K for 4 hours, the SA-FLB/B mixed solution was passed through a gel filtering column (Superose 12, Pharmacia, bead size: 10–11 μm, column size: 1.2×30 cm, number: 12) to be separated into sufficiently reacted SA and unreacted (or insufficiently reacted) SA. A solution of 10 mM of ammonium carbonate or phosphate (containing no NaCl) was used as a developer liquid (mobile phase). The measurement was conducted on the prepared specimen (the substrate 20 with the above-described fluorescent substance applied thereto) in the next two days since the lifetime of the SA/B complex is about 2.9 days.

The DFL (Exinton) is used to estimate the size of liquid droplets to be atomized. A $2.3\times10^{-5}$ M-DFL solution is atomized onto the silicon wafer (the substrate 20), and the substrate was mounted on the device of FIG. 2. While the laser beam was irradiating the substrate, a size of an area ($pixel^2$) where fluorescence was generated was measured by the photon counting system A. It should be noted that the sensitivity of the detector was lower than that used in the photon counting system A, the light source was a halogen lamp, and one pixel was 0.3 μm in the droplet size measurements. On the assumption that a contact angle of the liquid droplet was 90° the size of the area is converted into a volume of the semispherical liquid droplet 22a (FIG.3).

These fluorescent molecules, FLB+SA and DFL were used in consideration of biological and photophysical applications. The first substances to be measured (SA, FLB, B) are useful for applications involving immunoassay and DNA sequence. The second substance to be measured (DFL) is useful for applications involving photophysical studies.

The technique of forming a SA–FLB complex is based on a stoichiometric complicated composition of SA and FLB/B.

The number of SA molecules bonded at four sites is measured by computing a ratio of light absorptions (A(489), A(280)) with respect to 489 nm wavelength and 280 nm wavelength. Light absorption at 489 nm is only for FLB, and light absorption at 280 nm is only for FLB and B. B(biotin) does not absorb light in a 200–900 nm range. But Beer's law is not satisfied in a state where both SA and FLB are present (3–12 µM in 10 mM triethanolamine/HCl, pH=8.42).

Figure 5:
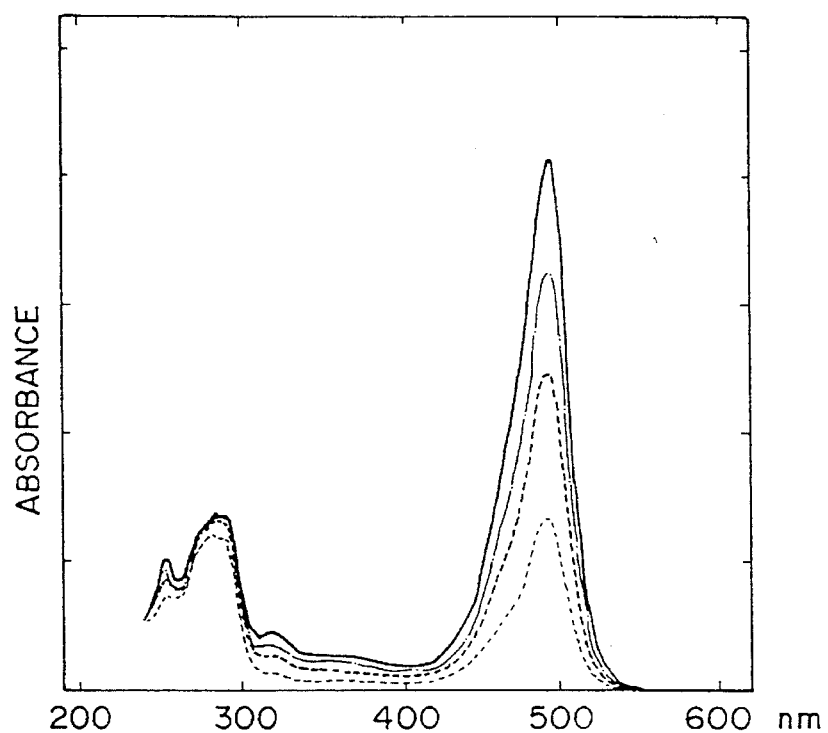
FIG. 5 is a view of an absorption spectrum of a SA-FLB/B mixed solution.

FIG. 5 shows an absorption spectrum of FLB/B mixed with SA. The spectrum is for compounds of FLB/B and SA having a ratio of 4:1. The spectrum was measured without column chromatography. In addition to the fact that the spectrum does not comply with Beer's law, as shown in FIG. 6, the half-value width of 489 nm increases with the increase of the FLB.

In FIG. 5, the measurement was conducted on a mixture of FLB/B and SA dissolved in a 10 mM triethanol amine/HCl solution at 296K. A mole ratio between the FLB/B and the SA is 4:1. In this range, d-biotin does not absorb light. The light absorption near 280 nm is mainly due to tryptophan in the SA. In FIG. 6, black plots mean that A (280) does not linearly increase with an increase in concentration of the FLB. White plots mean that a half-value width at a 489 nm peak widens with an increase in FLB concentration.

Figure 6:
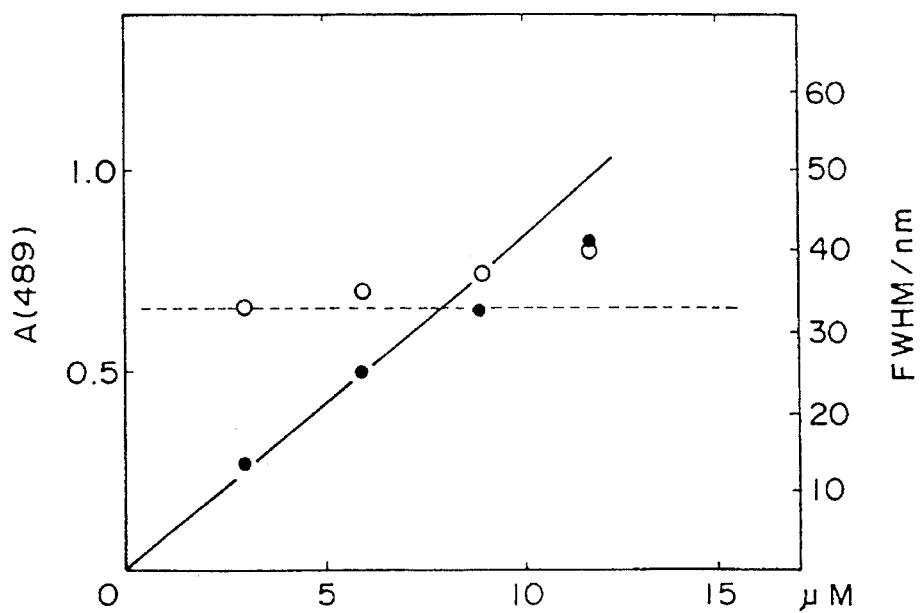
FIG. 6 is a view showing that the mixed solution of FIG. 5 does not follow Beer's law.
Figure 7:
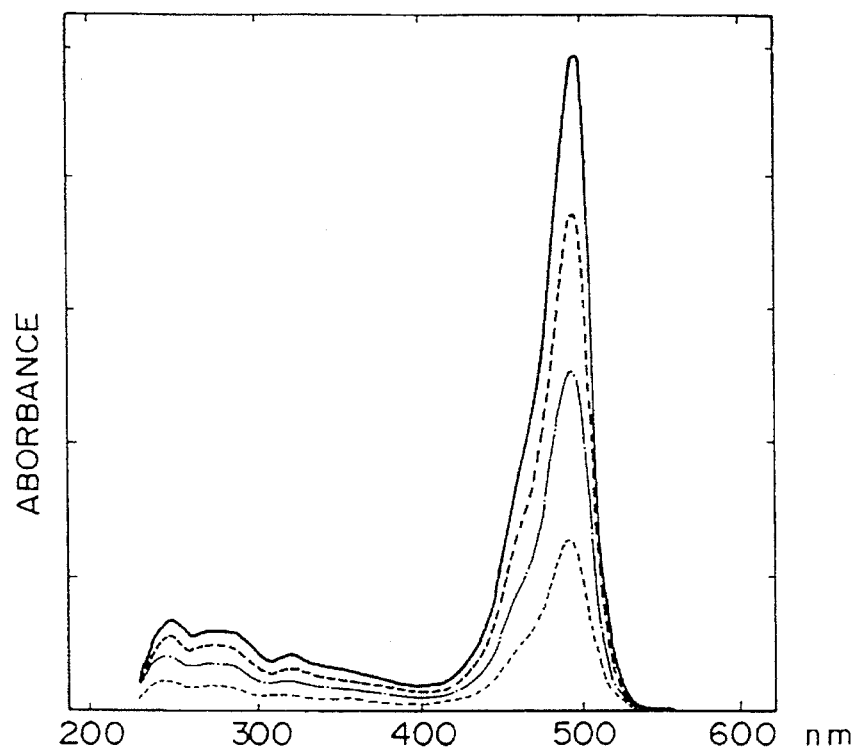
FIG. 7 is a view of an absorption spectrum of a SA-FLB solution.
Figure 8:
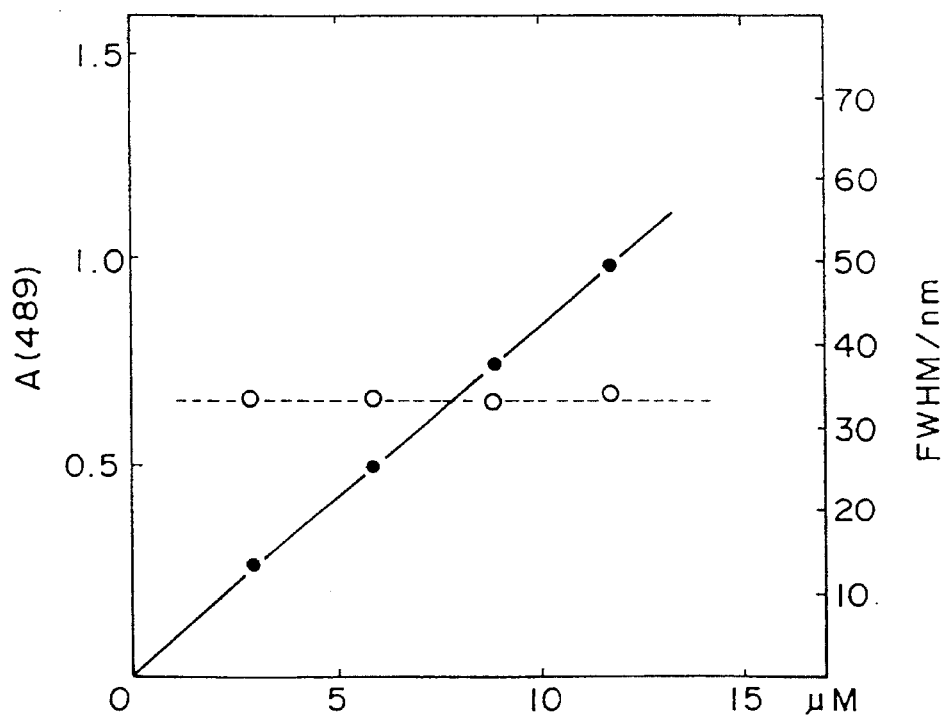
FIG. 8 is a view showing that the mixed solution as shown in FIG. 7 follows Beer's law.

FIGS. 7 and 8 show that a complex with only FLB follows Beer's law, and no expansion of a half-width value takes place in the same concentration range as in FIGS. 5 and 6. The number of the FLB bonded with SA can be determined by referring to a ratio between A(489) and A(280) in which the FLB has small contribution. The FLB/B bonding causes a red shift (shift to a shorter wavelength) of tryptophan near 289 nm. Based on the above, and on the assumption that the FLB/B and the SA in a mixed solution are completely bonded with each other, a ratio between A(489) and A(280) is given in FIG. 9. Based on the ratio, the number of the FLB can be estimated.

To stoichiometrically react SA with FLB/B, a suitable reaction time is important. The reason for this is not known. The reaction solution was let to stand overnight or longer, and the number of FLB/B bonded to SA decreased. A ratio between A(493) and A(280) depends on the fraction number of chromatography. Black marks in FIG. 9 indicate fractions with maximum ratios between A(493) and A(280), and these fractions were used. Ratios of 4FLB, 3FLB/B, 2FLB/2B, and FLB/3B considerably agree with a ratio, as a standard value, in the case where FLB/B and SA are mixed exactly in a mol ratio of 4:1. But a ratio of 3FLB/B apparently disagrees with the ratio as the standard value, and different ratios were obtained every time the above-described solution was prepared. A possible reason for this is that the FLB/B separates from the SA in chromatography.

Figure 9:
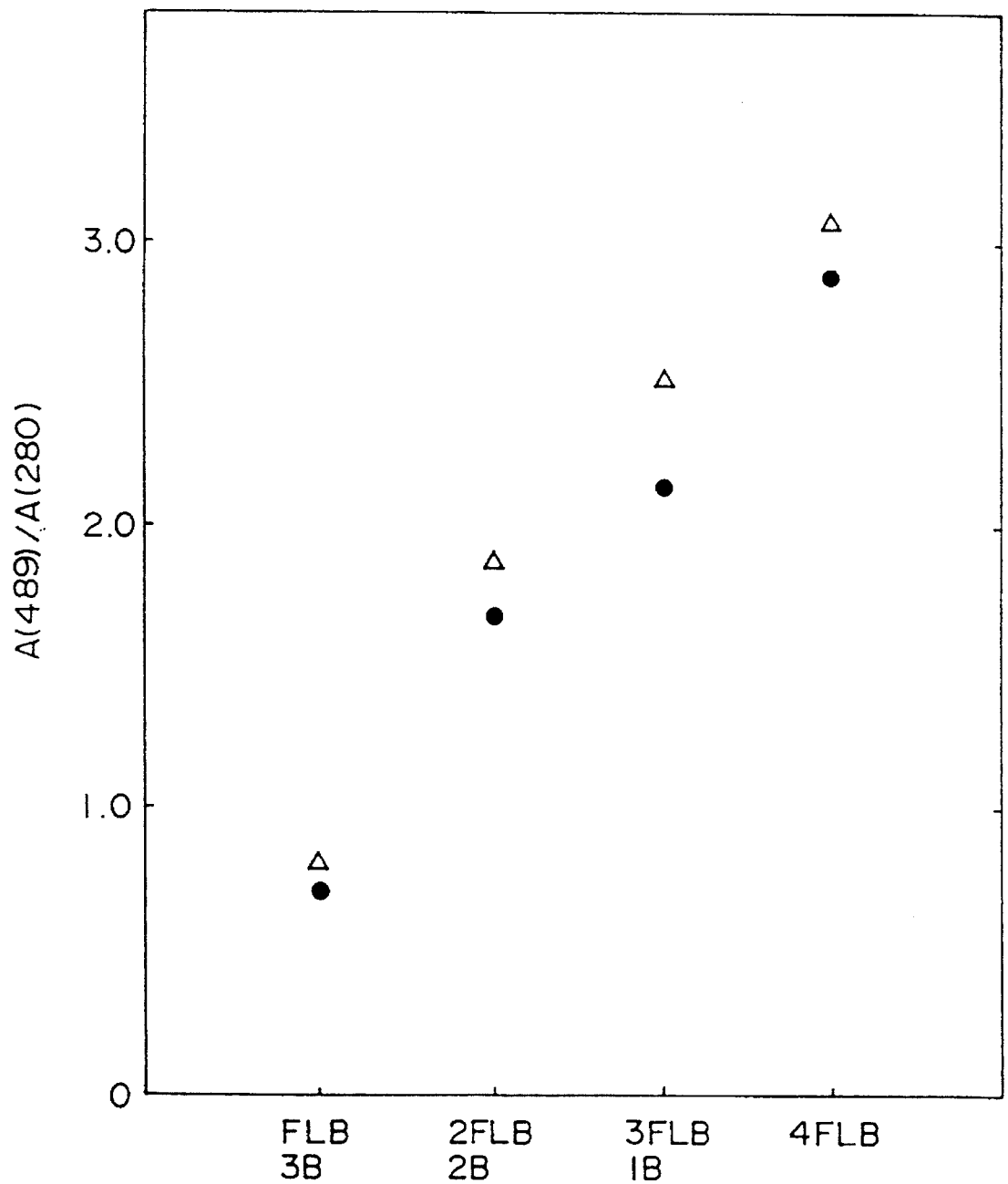
FIG. 9 is a view showing that the number of FLB/B bonding with SA is estimated by a comparison of the experimental data (•) with the standard sample (Δ).

FIG. 9 shows that the number of FLB/B bonded with SA can be calculated based on an absorption A(489) at 489 nm, and an absorption A(280) at 280 nm. Only FLB contributes to A(489), while A(280) includes contributions from SA and FLB. Estimations of A(489)/A(280) were conducted at various ratios between SA and FLB/B. Black plots indicate that FLB/B-SA mixture from chromatography was used, and white triangular plots indicate that mixing ratios of the SA and the FLB/B were exactly 1:4. The latter was used as a standard value for determining the number of the FLB bonded with the SA.

It is shown that fluorescent molecules at high concentration in water do not closely comply with Beer's law. According to some past studies with organic dyes, it has been found that the absorption spectrum varies depending on the concentration. Foster and Konig report that is has been found based on changes of absorption spectra of some organic dye molecules (fluorescent molecules) containing a fluorescent substrate in water that the organic dye molecules form dimers at high concentration ($10^{-3}$–$10^{-1}$M). Koizumi and Mataga report a change of absorption spectrum in an aqueous solution containing fluorescent molecules in the presence of electrolytic polymers. Based on these studies, it is considered that changes of the spectra are caused by the cohesive effect of the fluorescent molecules to the polymers. Considering these past studies and the bonding between SA and B due to their high affinity, it is considered that similarly sufficient local adhesion effects of FLB to SA can be present. This is further optical evidence of the interaction between SA and FLB. For example, bovine serum albumin, which has no affinity with FLB, causes no changes to FLB spectrum.

Figure 10:
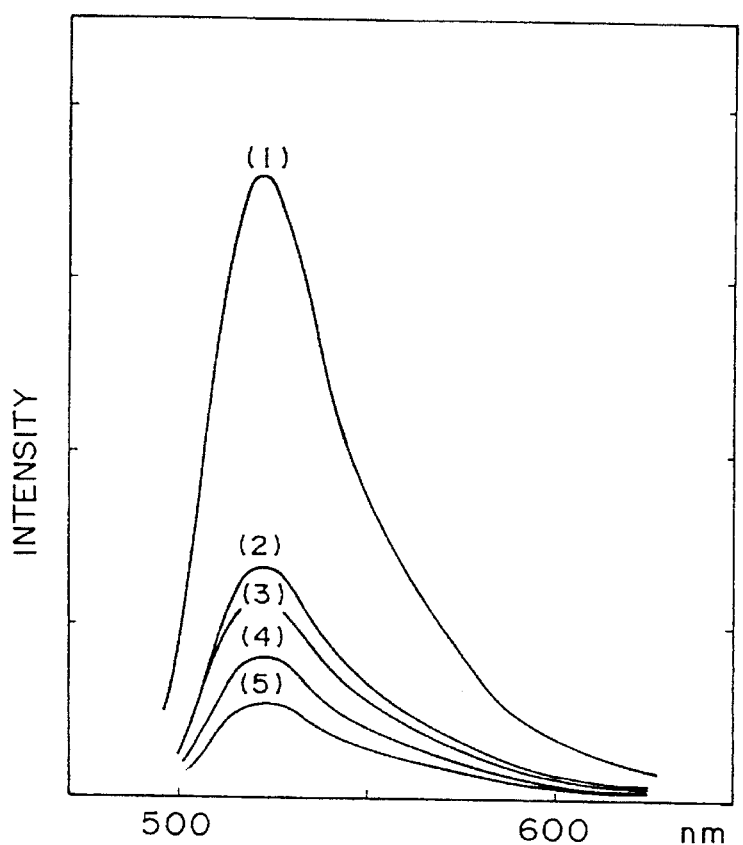
FIG. 10 is a view of fluorescence spectra of respective solutions of (1) FLB alone, (2) SA-FLB/3B, (3) SA-FLB/2B, (4) SA-FLB/B, and (5) SA-4FLB.
Figure 11:
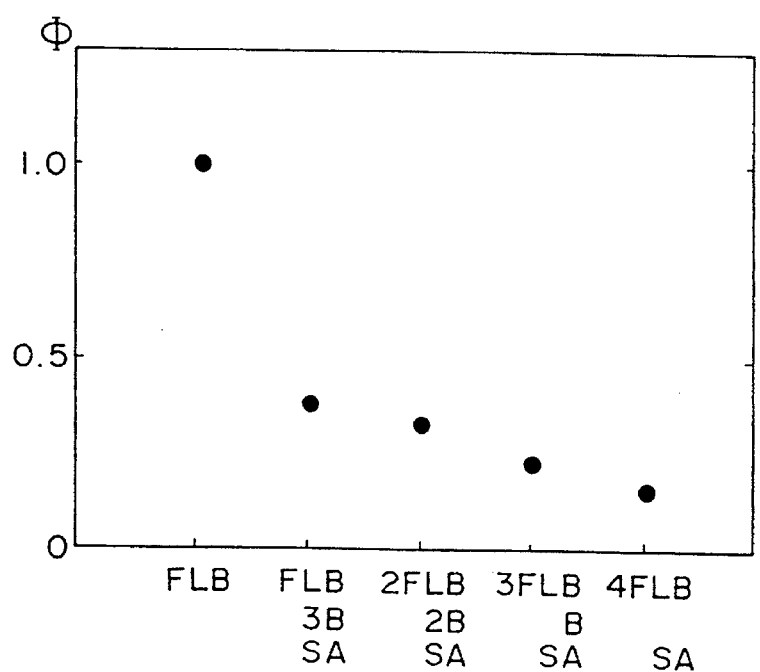
FIG. 11 is a view of changes of relative fluorescence quantum yield of the respective solutions as shown in FIG. 10 depending on SA and the number of FLB.

Then, a fluorescence spectrum and a relative fluorescence quantum generation ratio of FLB bonded with SA were measured. Taking into consideration abnormal behaviors of the absorption spectra, it is considered that the fluorescence characteristic of FLB is affected from bonding with SA. FIG. 10 shows fluorescence spectra of (1) FLB alone, (2) FLB/3B bonded with SA, (3) 2FLB/2B bonded with SA, (4) 3FLB/B bonded with SA, and (5) 4FLB bonded with SA (the bonding with SA was caused by dissolving with a 10 mM triethanol amine/HCl at pH 8.42 and 296K). The contours of the spectra are the same and the peaks are not shifted. But when the FLB first bonded with the SA, the intensity considerably decreased as the FLB continued bonding. FIG. 11 shows the calculated results of the relative fluorescence quantum generation ratios of (1) to (5) attributed to SA. Fluorescence due to quenching of the SA shows that there are extinction reactions between the amino acid of SA and FLB. The mechanism of fluorescence due to the quenching depends on the number of FLB and is considered the same as the self-quenching (which was reported in the above-described past study) by aqueous solutions containing fluorescent molecules.

Considering the above-described invention, a selection of suitable fluorescent molecules was conducted based on the results of FIGS. 10 and 11. Since a fluorescence quantum generating ratio and a fluorescence coefficient decrease with the number of the FLB, only SA-FLB/B (monomer) can be measured for confirming a detection of the number of molecules. In view of this, monomers are used in detecting the number of fluorescent molecules.

According to this invention, it is necessary that one liquid droplet contain a small number of fluorescent molecules in a molecule-group. Since the number of fluorescent molecules follows the Poisson distribution in the liquid droplet, the number of fluorescent molecules in the liquid droplet can be calculated with the Poisson distribution. The inventors prepared a highly purified solution containing DFL and caused the DFL to adsorb on a silicon wafer in fine liquid droplets by an ultrasonic humidifier to measure the droplet size (volume) and the number of fluorescent molecules in the one liquid droplet. The respective horizontal axes in FIGS. 12 to 14 show distributions of areas on the silicon wafer 20 occupied by one liquid droplet for 10-second, 7-second, and 3-second periods of atomizing time. Frequencies (the number of liquid droplets) for sizes of areas (in pixel$^2$ unit, 1 pixel=0.3 µm) are shown. Positions of the peaks are slightly shifted for the longer atomizing periods; however, contours of the distributions and the positions of the peaks in the respective contours are independent from the atomizing periods of time. Since a maximum peak is about 30–40 pixel (3–4 μm ), the number of fluorescent molecules in one liquid droplet is 1.00–1.56 for 1.0 nm/l concentration of the solution.

Liquid droplets having a very small number of molecules in a molecule-group are affixed to the substrate 20 (silicon wafer). Then 100 or more light emitting areas on the substrate 20 were measured by the device of FIG. 2. Their fluorescence intensities and the frequencies of fluorescence spots of the intensities were plotted.

The number of fluorescence photons per unit period of time, which were generated from a local area on the substrate 20 with excitation light irradiated thereon, was used as a quantized fluorescence intensity. A distribution of frequency of appearance of the fluorescence photons is formed on a part of a two-dimensional image corresponding to the local area on the substrate 20. An area with a higher frequency of appearance of the fluorescence photons in the distribution of frequencies of appearance of the fluorescence photons is a fluorescence spot corresponding to the molecule-group in the local area. Based on the location of the spot, the location of the molecule-group (preferably four molecules or less) can be identified.

Since the fluorescence intensity has a specific value corresponding to the number of fluorescent molecules, the number of fluorescence photons is counted by the above-described photon counting system A to measure, based on the counted value, the number of fluorescent molecules in one fluorescent spot (2-D photon counting method). The 2-D photon counting method is described in T. Hayakawa: Image Analysis in Biology, ed. D.- P. Hader, Chap. 5, pp. 75–86 (CRC Press, Boca Raton, 1992).

Figure 15:
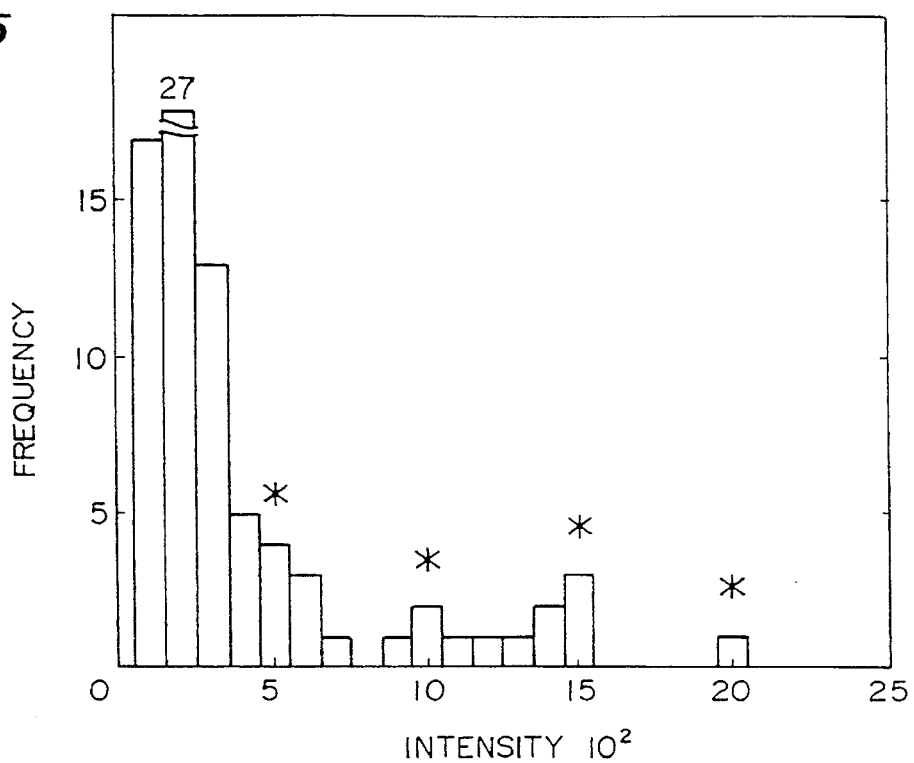
FIGS. 15 and 16 are views of fluorescence intensity distributions (relationships between the number of fluorescence photons per unit period of time and the appearance frequency of the photons) of SA-FLB/3B mixed solution. The intensity is relative quantity, not the actual number of photons.
Figure 16:
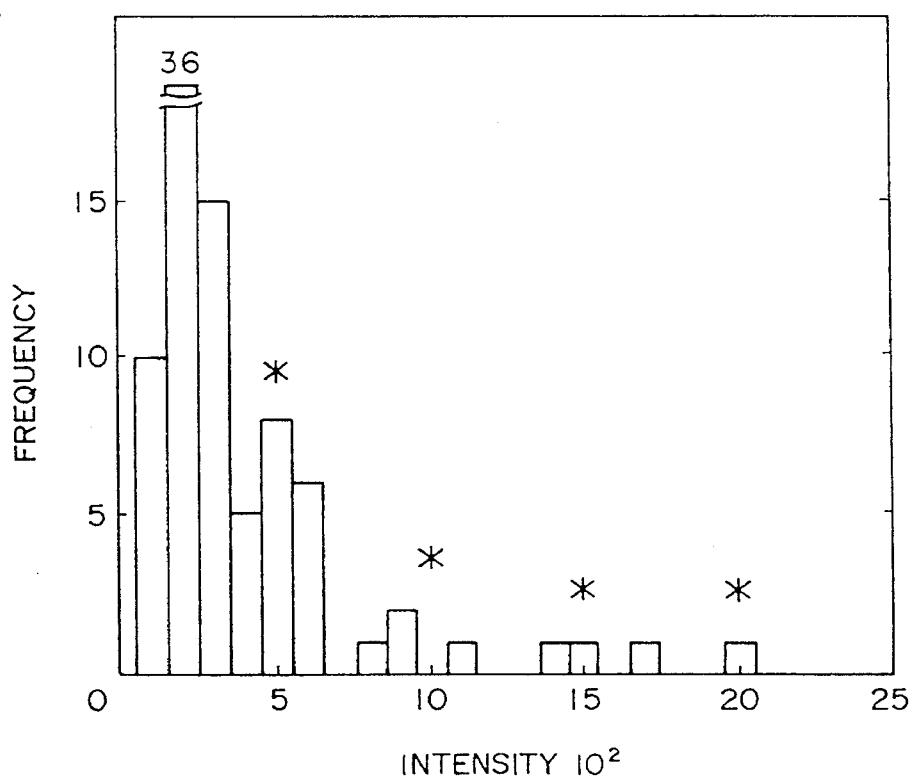
Figure 17:
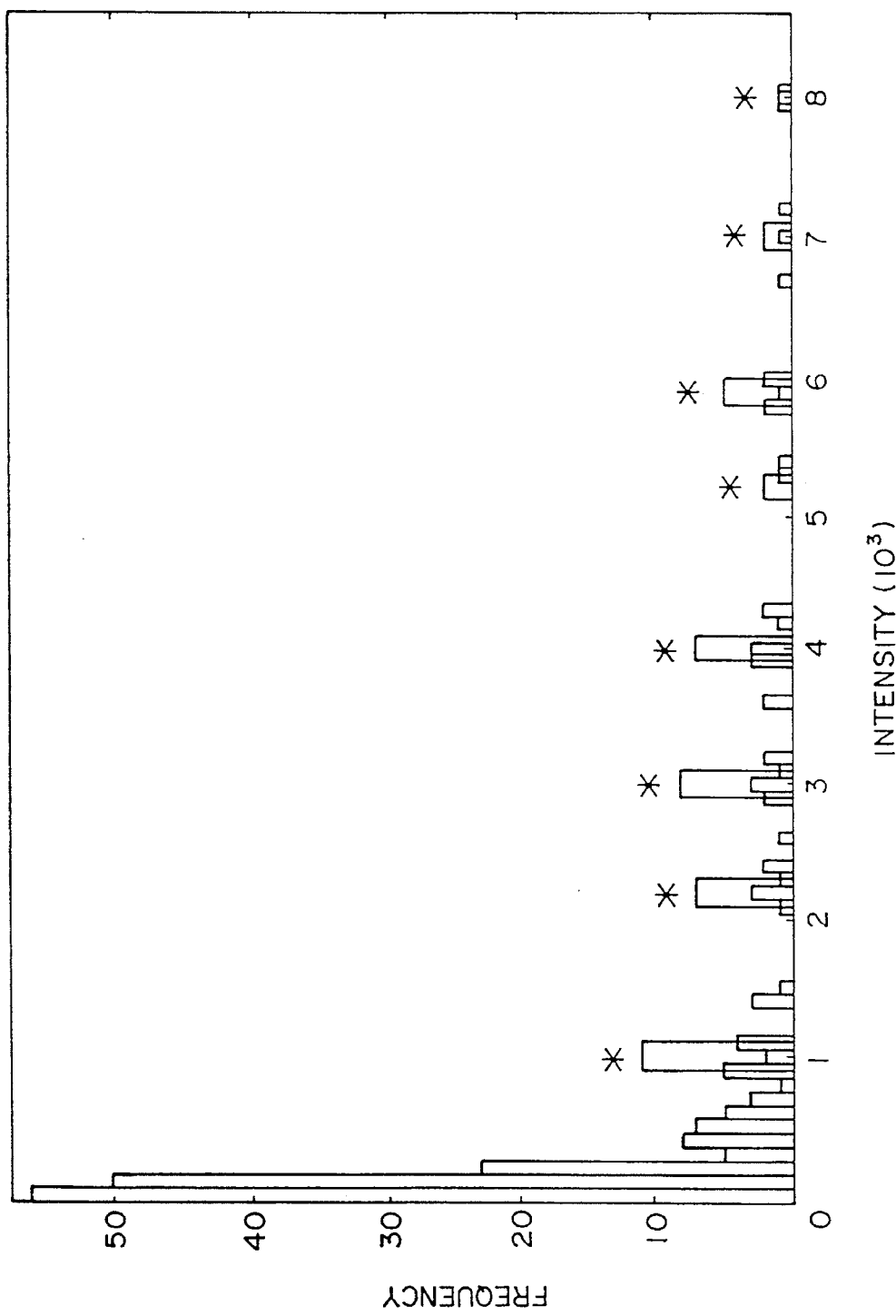
FIG. 17 is a view of a fluorescence intensity distribution (relationship between the number of fluorescence photons per unit period of time and the appearance of frequency of the photons) of a solution of DFL alone. The intensity is equal to the number of photons in this figure.
Figure 19:
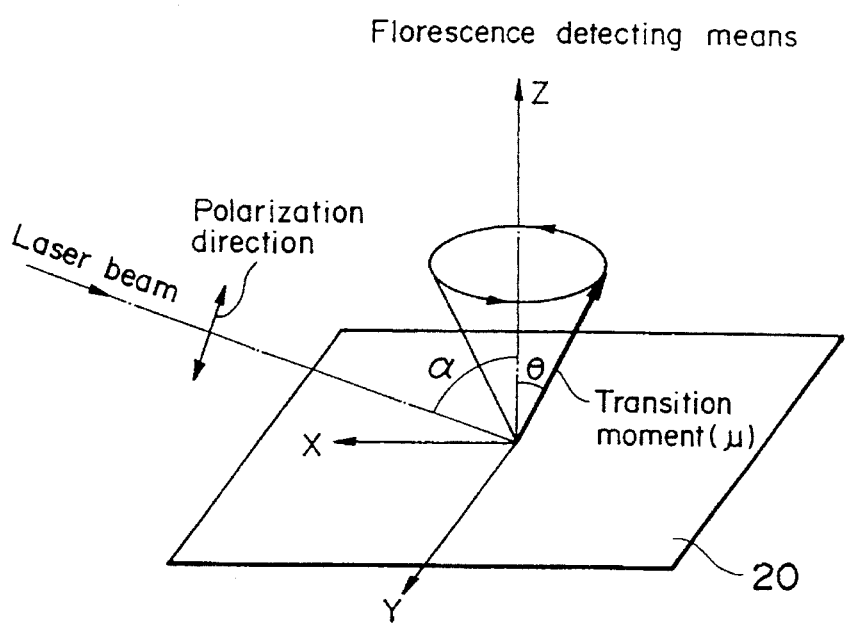
FIG. 19 is a view showing a relationship between the transition moment of DFL and the polarization of the 488 mm-laser beam.

Accordingly, the above-described fluorescence intensity is an absolute value based on the 2-D photon counting method. In FIG. 17, which will be explained later, the horizontal axis represents "the number of photons". In FIGS. 15 and 16, however, the horizontal axis represents the relative photon number. The results of FIGS. 15 to 17 have a 60-second data accumulating period of time. An excitation light intensity is 7 mW in FIGS. 15 and 16 and 20 mW in FIG. 17. A polarization direction of the laser beams in FIGS. 15 to 17 is parallel with the sheets of the drawings as shown in FIG. 19.

FIGS. 15 and 16 show the results of the measurement using FLB/3B bonded with SA on the entire surface of the substrate 20. (The optical microscope 42 was 40×, 0.55 NA.) Some peaks appear at every 500, which means that the fluorescence intensity is quantized. This measurement detects the number of fluorescence spots having from 1 to 4 sample molecules. Intensities smaller than 500 on the horizontal axis might be attributed to scattered light of 488 nm wavelength due to dust particles on the silicon wafer. A minimum peak value clearly appears at 500 on the horizontal axis in FIG. 16. This peak is considered to be attributable to the single SA bonded with the FLB/3B. FIG. 15 and FIG. 16 have different buffer liquids used in the column chromatography. In FIG. 15, phosphate (pH=7.5) was used alone, and in FIG. 16, ammonium carbonate was added (pH=7.5). These different results are believed to be caused by the suppression of optical noises, which are due to bases of the buffer liquid detected on the surface of the substrate 20 because of the volatility of the ammonium carbonate.

FIG. 17 shows the results of the measurement using DFL alone. (In this case, the optical microscope 42 was 100×, 0.75 NA). In this case as well, some peaks appear at every 1,000 and fluorescence intensities are quantized. The experiment in which water alone was atomized onto the silicon wafer 20 shows that the fluorescence intensities at 800 or less might be due to dust in the water. It can be affirmed that the fluorescence intensity at 1,000 is one of the single molecules of the DFL.

The frequency of the quantized fluorescence intensities can be calculated based on distributions of sizes of liquid droplets of FIGS. 12 to 14 and the concentration of the sample solution, and can be compared with experimental results in FIG. 17. The number of fluorescent molecules in one liquid droplet follows the Poisson distribution (Formula 1):

$$W(N) = \mu^N e^{-\mu}/N! \tag{1}$$

In Formula 1, W(N) represents the probability that N molecules are contained in one liquid droplet, and μ indicates the average number of molecules in one liquid droplet. Since some distribution occurs in the size of liquid droplets upon atomization, the actual number of liquid droplets is expressed by the following Poisson's equation with a weight of the distribution of liquid droplet sizes.

$$W(N) = \sum_\mu f(\mu) \mu^N e^{-\mu}/N! \tag{2}$$

$$\sum_\mu f(\mu) = 1 \tag{3}$$

Figure 18:
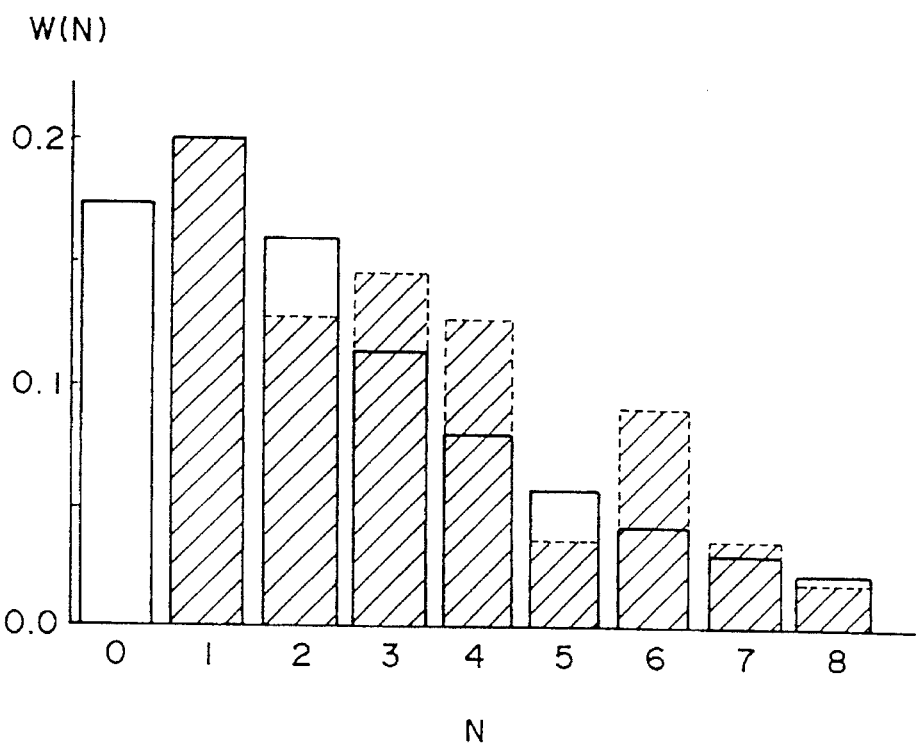
FIG. 18 is a view of theoretical values W(N) of a quantized fluorescence intensity distribution and the measured distribution of DFL (shaded) from FIG. 17.

In Formulas 2 and 3, f(μ) represents a rated weight coefficient and is calculated based on the respective size distributions of liquid droplets of FIGS. 12 to 14. FIG. 18 shows the calculation results of W(N) together with the measured results (shaded) of DFL (both data are normalized at frequency of N=1). These results are consistent, which means that the number of fluorescent molecules in each fluorescent spot can be detected.

Next, the data of FIG. 17 obtained by using the suitable fluorescent molecules DFL for theoretical studies will be quantitatively compared with the number of observable fluorescence photons by using parameters of excitation light intensities, fluorescent molecule light absorption and emission, fluorescence measuring detectors or optical components, and others.

The above-described "86 Proc. Natl. Acad. Sci. USA 4087–91 (1989)" contains a relevant description in connection with this evaluation method.

An excitation light (wavelength: 488 nm, output: 20 mW) is irradiated to the surface of a silicon wafer 20 in a 300 μm diameter (it is defined that the laser beams have a Gaussian space intensity distribution and a diameter which yields a $1/e^2$ intensity). An excitation light intensity ($I_{ex}$) is defined by:

$$I_{ex} = 2.37 \times 10^{19} (\text{Photons/sec/cm}^2).$$

A fluorescence photon number ($I_{abs}$) emitted by one fluorescent molecule per second is given as follows when a molecular light absorption coefficient is represented by ε:

$$\begin{aligned} I_{abs} &= 3.8 \times 10^{-21} \cdot \epsilon \cdot I_{ex} \\ &= 3.8 \times 10^{-21} \times 9 \times 10^4 \times 2.37 \times 10^{19} \\ &= 8.105 \times 10^3 (\text{photons/sec/molecule}) \end{aligned}$$

where a molecular light absorption coefficient ε at a disodium fluorescein (DFL) excitation light wavelength (488 nm) was $9 \times 10^4$/cm/M.

A fluorescence intensity ($I_f$) is calculated by multiplying this value $I^{abs}$ by the fluorescence quantum yield. That is, since the fluorescence quantum yield of disodium fluorescein is 0.95, the fluorescence intensity $I_f$ is given as follows:

$$I_f = I_{abs} \times 0.95 = 7.69 \times 10^3 \text{ (photons/sec/molecule)}.$$

Furthermore, when the data-accumulating time is 60 seconds, the total number of fluorescence photons ($I_{tot}$) generated from one fluorescent molecule is given as follows:

$$I_{tot} = I_f \times 60(\text{sec}) = 4.61 \times 10^5 (\text{photons/molecule}).$$

On the other hand, efficiency of detecting fluorescence photons is evaluated using known parameters as follows:

$$\begin{aligned} I_{abs} &= 4.61 \times 10^5 \times 0.12 \times 0.563 \times \\ & \quad 0.08 \times 0.60 \times 0.73 \times 1.4 \\ &= 1.53 \times 10^3 (\text{photons/molecule}) \end{aligned}$$

where a quantum yield of the photocathode of the photon counting camera is 0.12 at the fluorescence maximum (520 nm), and the upper limit of condensation efficiency of the objective (100×, 0.75 NA) is 0.56 (=$0.75^2$), quantum efficiency ($\eta_1$) is 12% around 520 nm, available transparency ($T_1$) is 8% and the maximum fluorescence collection efficiency ($\eta_2 = NA^2$) is 56.3% of the objective, the transparency of the DFL fluorescence photons through the band-path filter and the dichroic mirror ($T_2$) is 60%, the enhancement of the fluorescence collection by the silicon wafers ($\eta_3$) is 140%, and the total transparency ($T_3$) of other optics between the objective and the photocathode in the photon-counting apparatus is 73%. Note that the surface of the silicon wafers are as smooth as a mirror, thereby improving fluorescence collection efficiency.

In FIG. 17, a minimum unit of the quantized fluorescence intensity is $10^3$ (photons). This is considered to be the number of fluorescence photons which can be measured from one fluorescent molecule. Thus, the number of the actually observed photons $10^3$ is consistent with the calculated result ($I_{abs} = 1.53 \times 10^3$ photons/molecule).

In the case that the polarization direction of the laser beam is parallel with the sheet of the drawing (X–Z surface) as shown in FIG. 19, the direction of transition moment of a fluorescent molecule to be measured is important.

When a direction of the fluorescent molecules are fixed on the substrate 20 and the fluorescent molecules are excited by light with a set polarization direction, the light excitation efficiency depends on the transition moment of the fluorescent molecules and the angle of the excitation light to the polarization direction. That is, when both are parallel with each other, the light excitation efficiency is maximum; by contrast, no excitation takes place when both are normal to each other.

When both form different angles for respective fluorescent molecules, the quantized fluorescence intensities (the number of fluorescence photons) in FIG. 17 will not be obtained. To understand the results of FIG. 17, it is necessary to consider that the respective fluorescent molecules are moving.

"PHYSICAL REVIEW LETTERS", Vol. 48, No. 7, pp. 478–481, 1982 and "CHEMICAL PHYSICS LETTERS", Vol. 114, No. 1, pp. 103–108, 1985 disclose that the dye fluorescence which has produced the results of FIG. 17 has a transition moment that makes a procession, as shown in FIG. 19, at 53°±2° to the vertical line with respect to the surface of the substrate 20. In this state, since the vertically polarized excitation light interacts with a z-axis component of the transition moment, constant excitation efficiency can be obtained with respect to all of the fluorescent molecules.

It is understood from the above that a fluorescence intensity proportional to the number of fluorescent molecules can be observed. In other words, fluorescence photons are counted, whereby, based on a count value, the number of fluorescent molecules in one fluorescent spot corresponding to one molecule-group can be determined. Thus the measurement of the number of fluorescent molecules on first and second substances was successful.

In the prior art, the background light has such a large effect that fluorescence from respective fluorescent molecules becomes buried in the background light and cannot be detected. But this invention provides a great breakthrough in that it has succeeded in making such detection possible. This invention will make great progress in automation of immunoassay, chromatography and DNA analysis by enabling super-high speed fluorescence analysis.

As described above, a single molecule can be detected by adsorbing fluorescent molecules on the surfaces of solid substrates at room temperature and detecting locations and the number of fluorescent molecules by a two-dimensional photon counting method. Locations of single molecules are detected by means of a conventional optical microscope, based on fluorescent spots at a limit of its resolution. Fluorescent spots are scattered in a field of the microscope. The number of molecules in a fluorescent spot is a very important factor in detecting single molecules and depends upon intensities of fluorescence from the fluorescent spot. According to the above-described method, one molecule is present in one fluorescent spot, whereby the detection of single molecules is enabled.

In the conventional wet-type detection in which fluorescent molecules to be measured are dissolved in a solvent, Raman scattering in the solvent (water or others) causes background noises, which makes the measurement very difficult. According to the method of this invention, single molecules can be adequately detected by selecting a suitable substrate. It is very convenient and effective to use an ultrasonic wave (created from ultrasonic humidifies or others) on the substrate. Salts deposited from buffer liquids are sometimes present on the substrate together with fluorescent molecules to be measured, and sometimes determine levels of background noises. Buffer liquids are not always necessary to prepare a specimen solution, but depend upon the kind of fluorescent molecules. Nevertheless, a buffer liquid has to be carefully selected.

Furthermore, fluorescent molecules to be measured are effectively adsorbed on the substrate, and the substrate can be used in other measurements and is usable in the measurement by, e.g., STM and ATM, which are microscopes with good space resolution. It is possible to use STM or ATM to confirm the presence of single molecules. Fluorescence from fluorescent molecules can be used as means for discriminating kinds of fluorescent molecules in accordance with the detection method of this invention. The method of the present invention can be one method for determining sequences of bases constituting a single fragment of nucleic acid. That is, the bases of DNA are cut off one-by-one from the end, using exonuclease III, and the bases are discriminated one-by-one. In this case, the bases are placed at predetermined positions on the substrate which are determined by a cut sequence.

U.S. Pat. No. 4,962,037 discloses that the base could be cut off sequentially from the end of a single fragment of nucleic acids by using a solution containing the above-described enzyme, exonuclease III.

Figure 20:
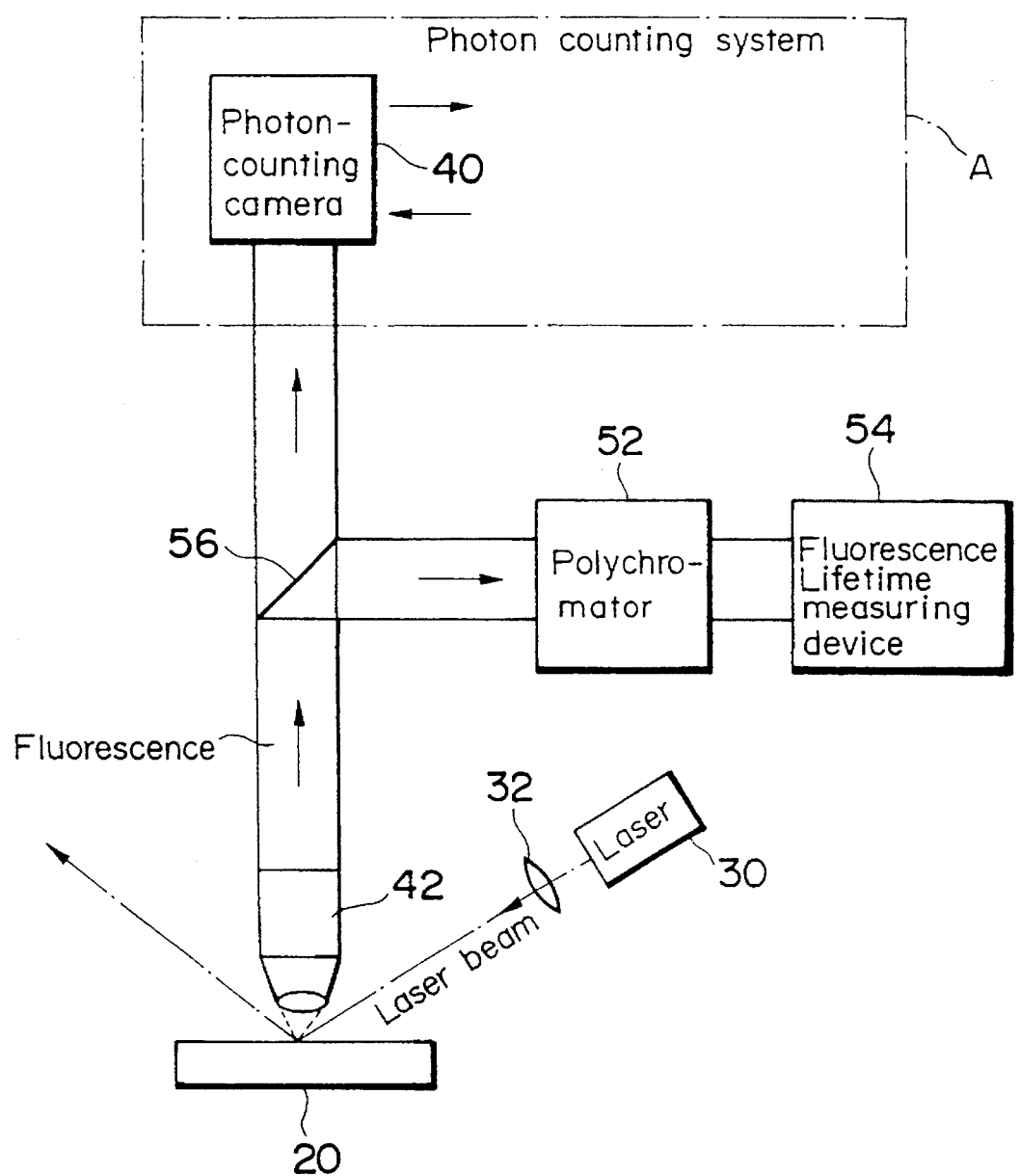
FIG. 20 is a diagrammatical view of the device for determining a sequence of bases of nucleic acid according to this invention.

FIG. 20 shows a block diagram of one example of the device used in the method for determining a sequence of bases of nucleic acid. This device comprises an excitation light source 30 for irradiating excitation light to a fine area on the surface of a substrate 20, and fluorescence detecting means for detecting fluorescence from bases at the irradiation position of the excitation light and for identifying kinds of the bases. The substrate 20 has a very high speculum degree (e.g., a silicon wafer). Nucleic acids composed of fluorescent molecule bases are adsorbed on the surface of the substrate by the above-described method. The substrate 20 is placed in a clean booth of class 1000 or less so as to be placed in a clean atmospheric air or inert gas (for example, Ne, Ar, etc. and an arbitrary complex gas of these elements).

This device may include the above-described photon counting system A to identify locations of the respective bases. The above-described moving means (FIG. 4) may be used for moving a local area (area for excitation light to be irradiated to) on the substrate 20.

Figure 21:
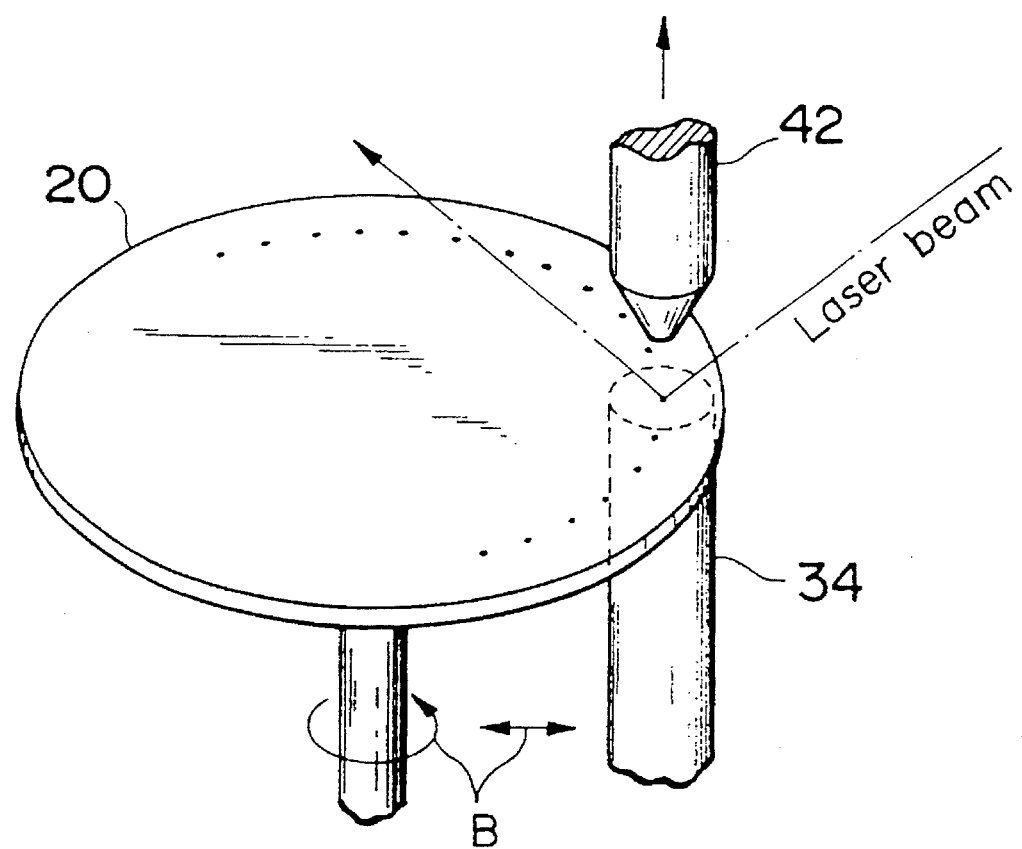
FIG. 21 is a view showing the irradiation by a laser beam in the device of FIG. 19 (including the cooling means).

As shown in FIG. 20, it is preferred that the excitation light source 30 can irradiate excitation light to a position on the substrate where bases are adsorbed. The excitation light source 30 is preferably a laser beam, since coherent laser beams are preferred. When the laser beam source has a wavelength of 300 nm or less, a pulse laser can be used. Excitation light (laser beams) is condensed by a lens 32. The excitation light source 30 is arranged in such a manner that the excitation light enters slantly as shown in FIG. 21, and reflected beams on the substrate 20 slantly propagate.

A photon counting system A may be included to identify locations of bases in a local area. In this case, as shown in FIG. 2, the system A is provided by an imaging/image synthesizing system (ARGUS 50 VIM 3) by Hamamatsu Photonics K. K. with an optical microscope 20 mounted thereon. The system A can two-dimensionally count fluorescent photons and perform two-dimensional photo- detection, whereby locations of the bases can be identified. The optical microscope 42 is for condensing fluorescence from the bases on the substrate 20 and has high magnifications (variable magnification). A photon-counting camera 40 is connected to an imaging/image analyzing system, so that signals are accumulated (fluorescence photon counting), images are processed, records are reserved, and images are displayed. Accordingly, the presence of respective bases can be detected.

A half mirror 56 is provided for branching fluorescence from the bases on the substrate 20, and branches a larger amount of light to a polychromator 52. The polychromator 52 measures fluorescence spectra. A fluorescence lifetime measuring device 54 measures lifetime of fluorescence. They are provided by a photomultiplier or a streak camera. These members identify kinds of the bases. In place of the half mirror 56, these members and the photon-counting camera 40 may be mechanically or optically changed over.

The position and rotation of the substrate 20 is controlled by the drive means as shown FIG. 4, so that an area on the substrate 20 can be positioned in the field of the optical microscope 42 and the photon counting camera 40. That is, as shown in FIG. 21, the substrate 20 is run at a constant speed in the direction indicated by B. A part of the substrate 20 near an area to be irradiated with excitation light is cooled by cooling means 34.

Fluorescence (autofluorescence) intrinsic to the kinds of the base at room temperatures is so feeble that it is necessary to multiply intensities of fluorescence of all the bases.

For example, "Photochemistry Photobiology", vol. 7, pp. 189–201, 1968 reports it was confirmed that an increase in autofluorescence of base A (adenine) can he obtained by lowering temperatures. "Photochemistry Photobiology", vol. 7, pp. 597–612, 1968 reports it was confirmed that an increase in autofluorescence of all the bases can be obtained by lowering temperatures.

Figure 22:
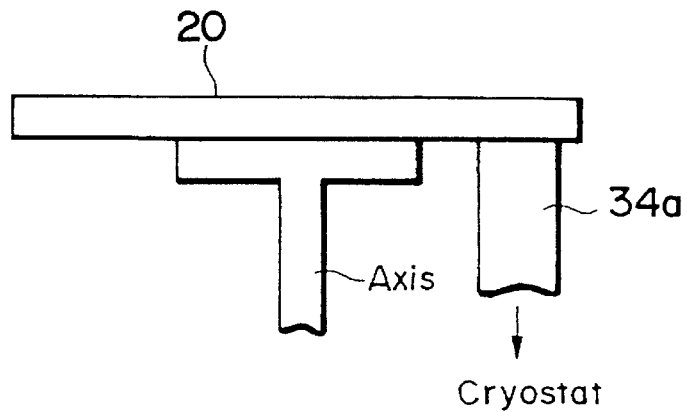
FIGS. 22–24 are diagrammatic views of specific structures of the cooling means 34 as shown in FIG. 21.
Figure 23:
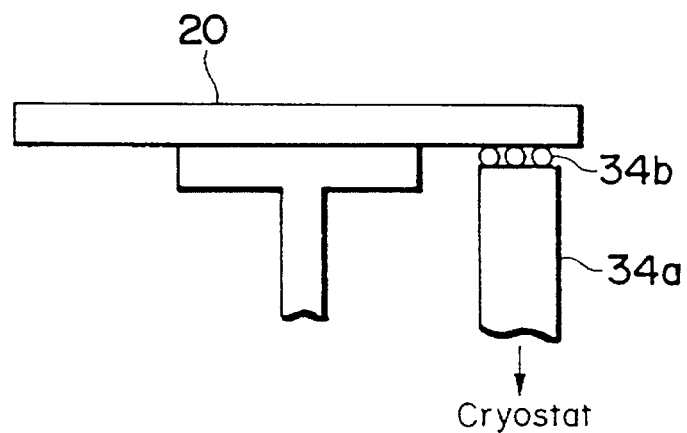
Figure 24:
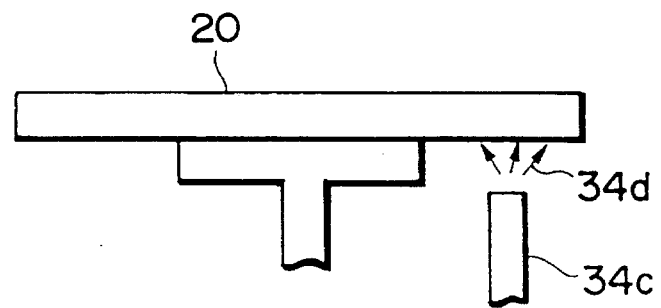

The cooling means is specifically provided by the cooling end 34a of a cryostat positioned on the underside of the substrate 20 (e.g., copper block) as shown in FIG. 22. Balls 34b with high heat conductance are positioned between the cooling end 34a and the substrate 20 as shown in FIG. 23. Cooling is achieved by blowing cooling gas (e.g., helium gas) 34d through a pipe 34c as shown in FIG. 24. This cooling has an effect of increasing fluorescence and suppressing dye deterioration in bases constituting many single components in a single fragment of nucleic acid.

Next, the method for determining a sequence of bases of nucleic acid using this device will be explained.

Figure 25:
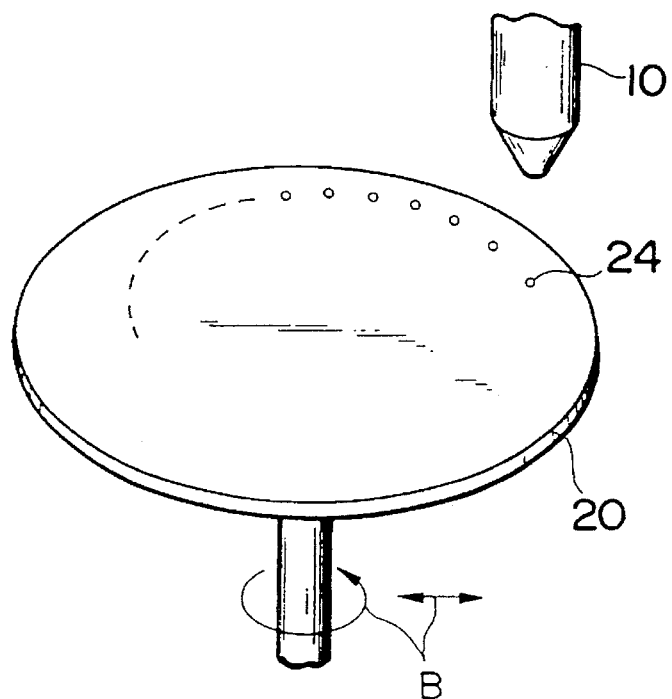
FIG. 25 is a view illustrating the application of bases in their sequences on the disc-shaped substrate 20.
Figure 26:
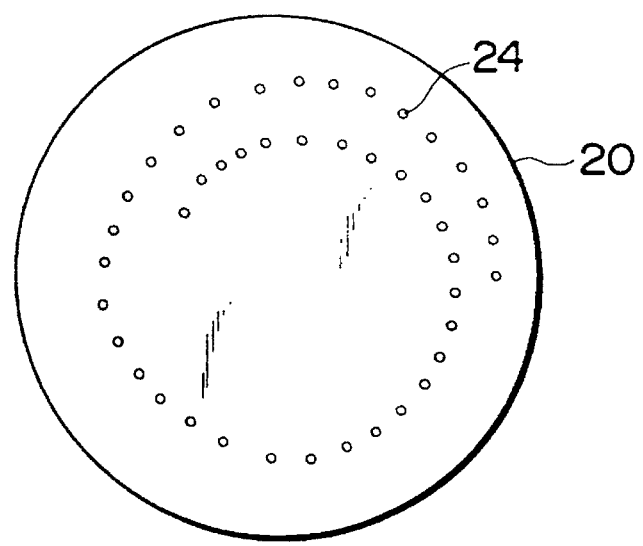
FIG. 26 is a view of the substrate 20 with adsorbed bases.

First, as shown in FIG. 25, liquid droplets 24 containing bases separated from a nucleic acid (e.g., DNA) are dropped onto the substrate 20 to prepare the substrate 20 with the bases adsorbed thereon (FIG. 26).

The substrate 20 is moved by the moving means as shown in FIG. 4. The substrate 20 is horizontally rotated so that the bases are circumferentially moved to be cut off radially inward and fall as liquid droplets 24 containing the bases. In this invention the substrate 20 is a disk. The moving means and substrate collectively produce the effect of downsizing the device.

It is necessary that the distribution of sizes of the liquid droplets be as uniform as possible. For example, "Anal. Chem., 1992, 64, 2914–2919" describes a liquid drop generating device which can form substantially 10 μm-diameter liquid droplets.

Figure 27:
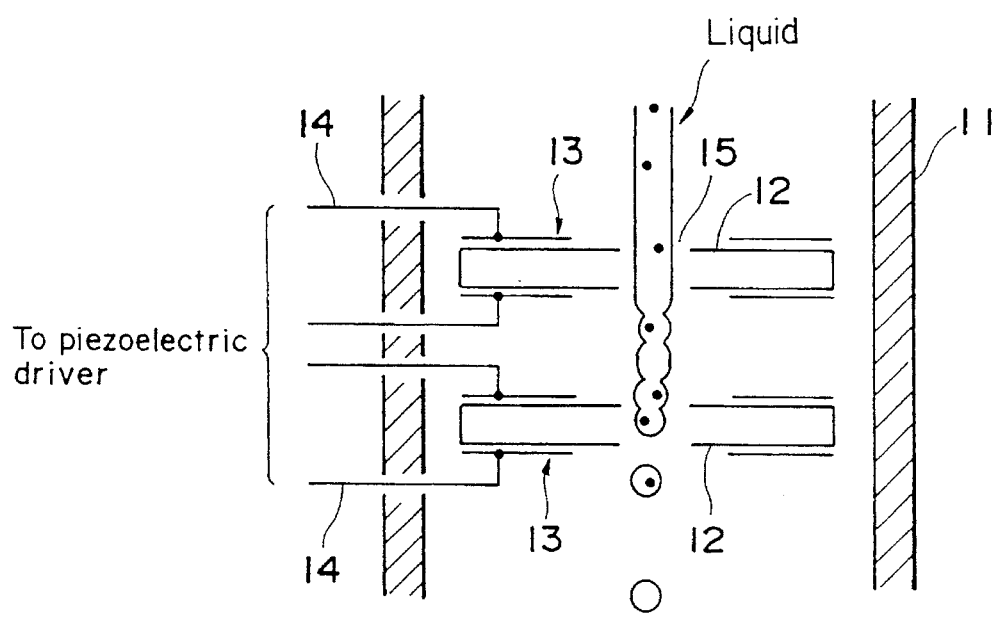
FIG. 27 is a detailed structural view of the flow cell in FIG. 25.

The flow cell 10 specifically has the structure shown in FIG. 27 and includes supersonic traps 12 in the main body 11. Each supersonic trap 12 has a piezo-element 13 and is connected to a piezo-drive circuit by a line 14. Liquid containing separated bases of DNA are caused to flow through a flow passage 15 of the flow cell 10, and the piezo-element 13 forms standing waves which separate and drop the liquids as shown in FIG. 27. On the other hand, the substrate 20 is rotated at a constant speed by the drive mechanism of FIG. 4 so that a position for a liquid droplet to be dropped thereon is deposited at the center thereof (FIG. 25). Dropped bases stick to the substrate 20 and run in the direction of the arrow C at a substantially constant interval so that one liquid droplet comes into a field of the optical microscope 42.

Nucleic acid is cut off sequentially from the end of a single fragment using a solution containing an enzyme, exonuclease III, as described in the immediately above-mentioned reference. The nucleic acid kept in good state at about 37° C. can be cut off at a speed of about 100 pieces/s using the above-described enzyme, and the liquid droplets in fine particles are dropped from the flow cell 10 at a speed of about 300 pieces/s. The frequency of the standing waves are adjusted in such a manner that the fine particles dropped from the flow cell 10 have an about 30 μm diameter, and taking account of Poisson's equation, one liquid droplet contains one base. Thus the substrate 20 with a spiral pattern of bases, with the bases deposited one after another can be prepared.

Idealistically, conditions which lower the possibility of one liquid droplet containing two or more bases are preferred (e.g., a preferred average number is 0.1 or less).

According to this invention, liquid droplets 24 containing bases and liquid droplets 24 not containing the bases are present on the substrate 20, since this is the best method for accurately recognizing a sequence of the bases.

Then, the substrate 20 with the liquid droplets 24 stuck to is air-dried to remove the solvent. Because it is very possible that heating or vacuum drying the solvent molecules will remove fluorescent molecules (bases) from the substrate 20, the solvent is naturally dried so that the fluoresent molecules are left on the substrate 20. Drying is effective to decrease Raman scattering from the solvent and suppress dye deterioration. The air-drying may be conducted together with cooling. The substrate 20 of silicon can be a good specimen. This is because dangling bonds are actively bonded.

The substrate 20 having the bases thereon is mounted on the device of FIG. 20, and the moving means of as shown in FIG. 4 is driven to bring a visual field of the optical microscope 42 near a position where a first liquid droplet to be measured is present. While laser beams irradiate the substrate 20, fluorescence from the bases is detected by the fluorescence photon counting system A, and a first one of the bases on the substrate 20 is observed to confirm that the base is within the visual field of the optical microscope 42. It is also confirmed that the base is one field piece. When a plurality of bases are present in the visual field of the optical microscope 42, the visual field of the optical microscope 42 is displaced, or a magnification is selected so that one base is present in the visual field. Pulsed laser beams are irradiated from the excitation light source 30 to the base to be measured to excite the same, and a fluorescence wavelength and a fluorescence lifetime are measured by the polychrometer 52 and the fluorescence lifetime measuring device 54.

The principle that different kinds of bases can be identified based on fluorescence wavelengths and fluorescence lifetime is disclosed in U.S. patent application Ser. No. 07/968,868, or European Laid-Open No. 0 556 509 A2.

On the surface of the substrate 20 on which fluorescent molecules are adsorbed, extremely little Raman scattering is observed and the background light has a small area. The laser beams from the excitation light source 30 are prohibited from entering the visual field of the optical microscope 42. The substrate 20 (silicon wafer) possesses a high speculum degree. Accordingly, the background light has a small effect. The background light especially has a smaller area in the reflected case in comparison to the transmitted case. As a result, although fluorescence from the respective bases is very feeble, the fluorescence can be measured without being hidden by the background light. Since it is almost impossible for the excitation light to be injected into the fluorescence detecting means 40 by the reflection thereof, the excitation light does not become a noise component even when the polychrometer 52 has imperfect cut-off characteristics.

Based on differences of the thus-obtained fluorescence wavelengths and fluorescence lifetimes, the respective bases can be discriminated between A, T, G and C, and a nucleotide in the field of the optical microscope 42 can be identified as A, T, G or C. The fluorescence detection may be conducted off-line to elongate a detection period. Then an irradiation area of the laser beams (i.e., the visual field of the optical microscope 42) is moved by the moving means as shown in FIG. 4 to a next base stuck to the substrate to similarly identify the kind of base. By observing the bases one after another, a sequence of a single fragment can be determined.

According to this invention, bases to be measured are stuck to the substrate. While positional information of the respective bases is obtained, the kinds of the bases are identified. The measurement can be repeated and used as a recording medium of nucleic acid.

In addition, the above-described embodiments can have variations.

For example, the substrate 20 is preferably a silicon wafer, but other semiconductors, insulators, or metals may be used as long as substantially the same high flatness and speculum are available. For example, aluminum and gold are vapor deposited films, but have disadvantages in that they are easily oxidized and are vulnerable to damages. Metal substrates coated with silicon oxides can be used as the substrates 20 if they have high speculum degrees.

Figure 28:
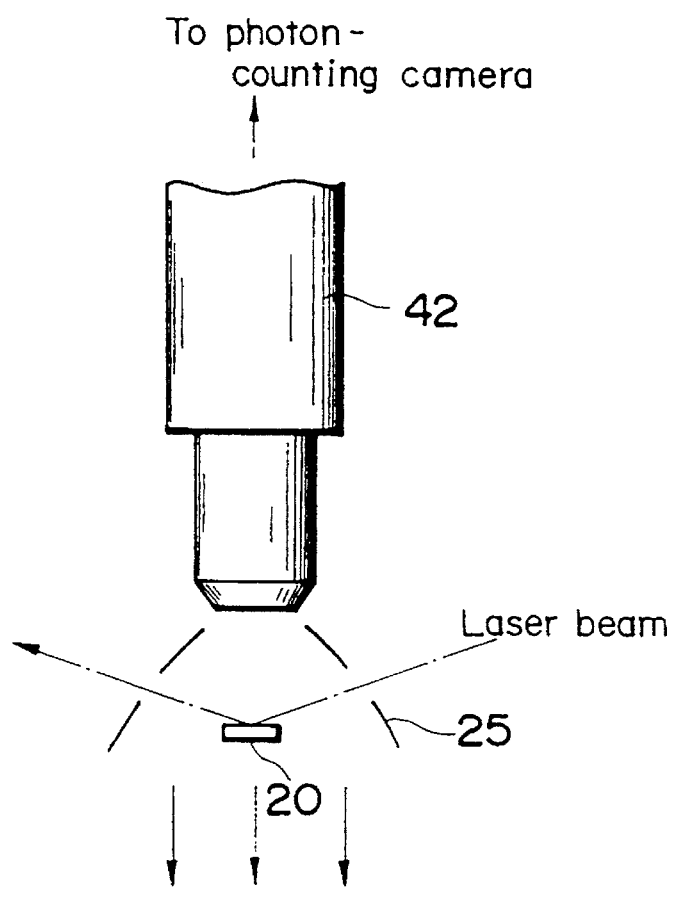
FIG. 28 is a diagrammatic view of an example of the device for determining a sequence of bases of nucleic acid according to this invention.
Figure 28:
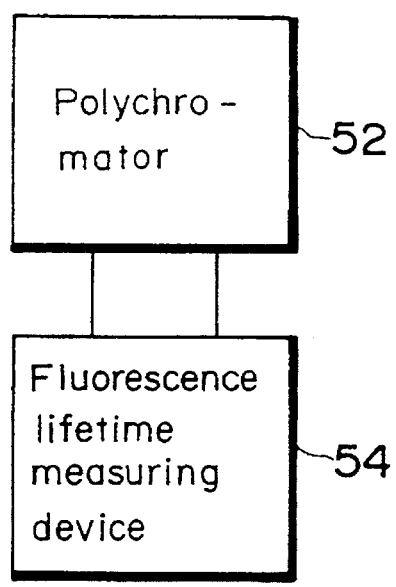

The optical microscope 42, the polychrometer 52, and the fluorescence lifetime measuring device 54 may be arranged as in FIG. 28. In this arrangement, a reflecting mirror 25 reflects fluorescence from fluorescent molecules (bases, etc.) to the polychrometer 52 and the fluorescence lifetime measuring device 54, whereby wavelengths and fluorescence lifetimes can be accurately measured.

A plurality of photon counting cameras 40 may be provided in the photon counting system A. When one detection fails, the detection may be repeated. This is because bases which have been stuck to the substrate 20 do not thereafter change their positions. Light emission or fluorescence detection can be repeated.

There are light emitting reagents that bond with bases A, T, G and C. Antibodies can be coated with these reagents to augment detection of the bases.

Figure 29:
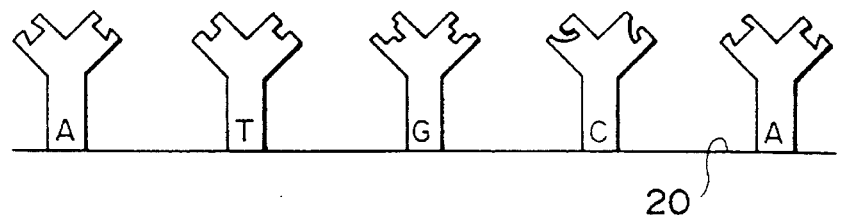
FIGS. 29–32 are pictorial views of the principle for luminescence detection for identifying kinds of bases (monoclonal antibodies applied to the substrate).
Figure 30:
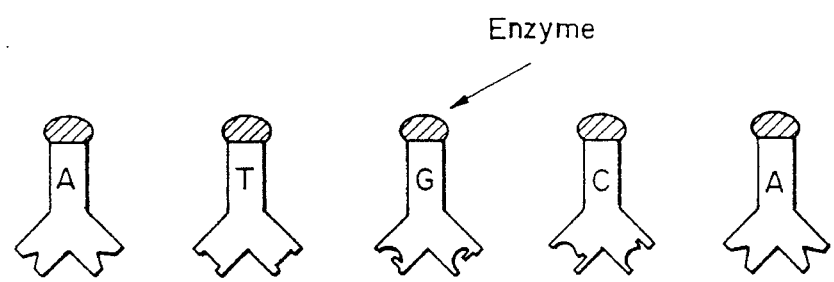
Figure 31:
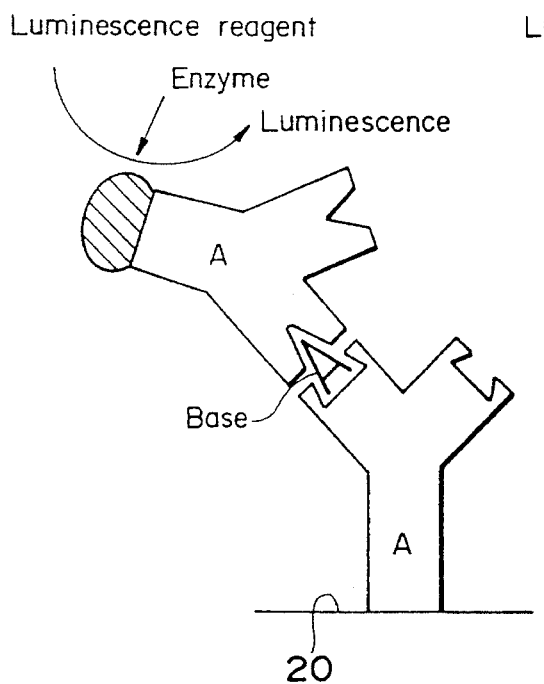
Figure 32:
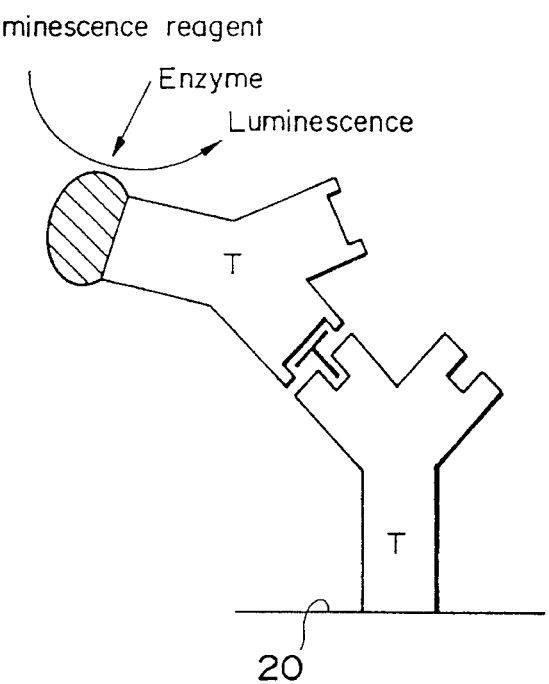

Monoclonal antibodies A, T, G and C, which comprise homogeneous molecules, have the characteristic of specifically bonding to bases A and C. These monoclonal antibodies are first applied to the substrate 20 (FIG. 29). Then, bases of nucleic acid are dropped by the flow cell 10 to the substrate 20. The bases A and C bond with their corresponding antibodies A and C. The luminescent antibodies A and C have respective luminescent enzymes as shown in FIG. 30 and the characteristic of specifically bonding with the bases A and C, respectively. The luminescent monoclonal antibodies A to C are placed on the substrate 20 and the surplus is rinsed off. As shown in FIG. 31, a monoclonal antibody A on the substrate 20 bonds specifically with the base A; further, a luminescent antibody A on the substrate 20 specifically bonds with the base A. As shown in FIG. 32, a monoclonal antibody T on the substrate 20 bonds with the base T; further, a luminescent antibody T bonds with the base T. Thus, by varying wavelengths of the respective enzymes, it is possible to discriminate the bases by detecting luminescence.

As described above, according to the method for determining a location of a molecule-group and the number of fluorescence molecules in the molecule-group, the background light can be sufficiently suppressed to directly detect fluorescence from a single fluorescent molecule (e.g., a base) to be measured. Accordingly, the quantized fluorescence can be observed, whereby the location and number of molecules sticking to the surface of the substrate can be detected.

According to the method and the device for sequencing bases of nucleic acid of this invention, fluorescence wavelengths and lifetimes of fluorescent molecules containing the bases on the surface of the substrate are measured after it is confirmed that the fluorescent molecules are in a single molecule state. Accordingly, bases contained in the single molecules can be correctly identified, and the bases are identified one after another, whereby sequence of the bases can be determined at high speed and without error.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

What is claimed is:

1. A device for determining a location of a molecule-group and the number of fluorescent molecules in said molecule-group comprising:

a light source for irradiating a local area on a flat substrate with excitation light, said local area having a molecule-group comprising an adsorbed fluorescent molecule; and fluorescence detecting means for detecting fluorescence photons generated by irradiating said local area on said substrate with excitation light, for identifying a fluorescent spot where said molecule-group is present based on a two-dimensional frequency distribution of said fluorescence photons, and for determining said number of said fluorescence molecules in said molecule-group by measuring the number of said fluorescence photons per unit period of time as a quantized fluorescence intensity of said molecule-group, measured in said fluorescent spot.

2. A device according to claim 1, wherein said fluorescence detecting means is disposed at a position which is out of an optical path of said excitation light irradiated from said light source and reflected light from a surface of said substrate.

3. A device according to claim 2, wherein said fluorescence detecting means includes an optical microscope for condensing said fluorescence in said local area on said surface of said substrate; and a photon counting system for counting said number of said fluorescence photons condensed by said optical microscope, and displaying an appearance frequency distribution of said fluorescence photons on a two-dimensional image corresponding to said local area.

4. A device according to claim 3, wherein:

said photon counting system forms an appearance frequency distribution of said fluorescence photons for said unit period of time by plotting a total number of fluorescence photons corresponding to a measuring position of said fluorescent photons on a two-dimensional image corresponding to said local area on said substrate, every time said fluorescence photons are detected by irradiating said excitation light; and said photon counting system identifies a fluorescent spot where said molecule-group is present, based on said appearance frequency distribution and determines said number of said fluorescent molecules in said molecule-group based on said number of said fluorescent photons measured in said fluorescent spot.

5. A device according to claim 3, wherein said optical microscope can change its magnification.

6. A device according to claim 2, wherein said excitation light includes a laser beam.

7. A device according to claim 1, further comprising moving means for relatively displacing said local area on said substrate.

8. A device according to claim 7, wherein said moving means includes an X-Y stage being movable horizontally to said fluorescence detecting means, and a rotary stage supported by said X-Y stage for fixing said substrate.

9. A device for determining a sequence of bases in nucleic acid comprising:

a light source for irradiating a a local area having a base therein with excitation light, said local area being on a flat substrate holding a sequence of said bases of nucleic acid;

fluorescence detecting means for detecting fluorescence generated from said base present in said local area on said flat substrate and for identifying a kind of said base based on a wavelength distribution of said fluorescence and a lifetime of said fluorescence;

moving means for moving said substrate; and means for controlling said moving means so as to relatively move said local area on said flat substrate along said sequence of bases.

10. A device according to claim 9, wherein said fluorescence detecting means includes an optical microscope for condensing said fluorescence in said local area on said surface of said substrate; and a photon counting system for counting the number of fluorescence photons condensed by said optical microscope and displaying an appearance frequency distribution of said fluorescence photons on a two-dimensional image corresponding to said local area.

11. A device according to claim 9, wherein said fluorescence detecting means is disposed at a position which is out of an optical path of said excitation light irradiated by said light source and of a reflected light from said surface of said substrate.

12. A device according to claim 11, wherein said light source includes a laser device.

13. A device according to claim 9, wherein said substrate includes a silicon wafer.

14. A device according to claim 13, wherein said substrate is disk-shaped.

15. A device according to claim 9, wherein said moving means includes an X-Y stage being movable horizontally to said fluorescence detecting means, and a rotary stage supported by said X-Y stage for fixing said substrate.

16. A device according to claim 9, comprises cooling means for cooling said local area on said surface of the substrate.

17. A device for determining a sequence of bases in nucleic acid comprising:

a light source for irradiating a local area having a base therein with excitation light, said local area being on a flat substrate holding a sequence of said bases of nucleic acid;

fluorescence detecting means for detecting fluorescence generated from said base present in said local area on said flat substrate and for identifying a kind of said base based on a wavelength distribution of said fluorescence and a lifetime of said fluorescence;

moving means for respectively moving said local area on said flat substrate along said sequence of said bases; and cooling means for cooling said fluorescent molecule in said local area of said substrate, wherein said substrate is positioned between said fluorescence detecting means and said cooling means.

* * * * *